(12) United States Patent
Vipperman et al.

(10) Patent No.: US 12,042,343 B2
(45) Date of Patent: *Jul. 23, 2024

(54) ADJUSTABLE RETAINING ARM SYSTEM

(71) Applicants: University of Pittsburgh—Of the Commonwealth System of Higher Education, Pittsburgh, PA (US); UPMC, Pittsburgh, PA (US)

(72) Inventors: Jeffrey S. Vipperman, Pittsburgh, PA (US); Christopher Michael Dumm, Verona, PA (US); Garth Abraham Elias, Pittsburgh, PA (US); Tyler Michael Ferris, Canfield, OH (US); Mark Scaife, Pittsburgh, PA (US); Peter David Allen, Pittsburgh, PA (US)

(73) Assignees: University of Pittsburgh—Of the Commonwealth System of Higher Education, Pittsburgh, PA (US); UPMC, Pittsburgh, PA (US)

( * ) Notice: Subject to any disclaimer, the term of this patent is extended or adjusted under 35 U.S.C. 154(b) by 99 days.

This patent is subject to a terminal disclaimer.

(21) Appl. No.: 17/862,078

(22) Filed: Jul. 11, 2022

(65) Prior Publication Data

US 2022/0346908 A1 Nov. 3, 2022

Related U.S. Application Data

(63) Continuation of application No. 16/480,926, filed as application No. PCT/US2018/016594 on Feb. 2, 2018, now Pat. No. 11,382,716.
(Continued)

(51) Int. Cl.
*A61B 90/50* (2016.01)
*A61B 17/00* (2006.01)
(Continued)

(52) U.S. Cl.
CPC ........ *A61B 90/50* (2016.02); *A61B 17/00234* (2013.01); *A61B 17/02* (2013.01);
(Continued)

(58) Field of Classification Search
CPC ......... A61B 90/50; A61B 34/71; A61B 90/30; A61B 90/35; A61B 90/361; A61B 90/57;
(Continued)

(56) References Cited

U.S. PATENT DOCUMENTS 3,858,578 A 1/1975 Milo
5,513,827 A 5/1996 Michelson
(Continued)

OTHER PUBLICATIONS

International Search Report and Written Opinion for related International Application No. PCT/US2018/016594, mailed May 17, 2018, 9 pages.

*Primary Examiner* — Aaron F Roane
(74) *Attorney, Agent, or Firm* — Klarquist Sparkman, LLP

(57) ABSTRACT

Disclosed adjustable retaining arm systems can include a multi-segmented, articulable arm that holds one or more interchangeable tools and can be made relaxed to set a desired position and made rigid to fix the desired position by adjusting tension in a cable running through the arm. The arm can quickly attach and detach from a support structure. The support structure include a cable tensioning system, sensors, control system, power system, etc. A user input device, such as a foot pedal or button on the arm, can be used by a surgeon to change the arm between relaxed and rigid states. The arm and attachable tools can be detachable, disposable and/or sterilizable, while other system components can remain mounted in a fixed location as the arm is removed and replaced. The arm can hold multiple tools in any desired orientation around subject work location.

20 Claims, 37 Drawing Sheets

Related U.S. Application Data

(60) Provisional application No. 62/453,608, filed on Feb. 2, 2017.

(51) Int. Cl.
*A61B 17/02* (2006.01)
*A61B 34/00* (2016.01)
*A61B 90/00* (2016.01)
*A61B 90/30* (2016.01)
*A61B 90/35* (2016.01)
*A61B 90/57* (2016.01)

(52) U.S. Cl.
CPC .............. *A61B 34/71* (2016.02); *A61B 90/30* (2016.02); *A61B 90/35* (2016.02); *A61B 90/361* (2016.02); *A61B 90/57* (2016.02); *A61B 2017/0023* (2013.01); *A61B 2017/00486* (2013.01); *A61B 2017/00973* (2013.01); *A61B 2034/715* (2016.02)

(58) Field of Classification Search
CPC .............. A61B 17/00234; A61B 17/02; A61B 2034/715; A61B 2017/0023; A61B 2017/00486; A61B 2017/00973
USPC .......................................................... 606/1
See application file for complete search history.

(56) References Cited

U.S. PATENT DOCUMENTS

| | | |
|---|---|---|
| 5,662,300 A | 9/1997 | Michelson |
| 6,866,628 B2 | 3/2005 | Goodman et al. |
| 7,828,808 B2 | 11/2010 | Hinman et al. |
| 8,187,279 B2 | 5/2012 | Livorsi |
| 11,382,716 B2 * | 7/2022 | Vipperman ............ A61B 90/57 |
| 2011/0028797 A1 | 2/2011 | Yee et al. |
| 2012/0157788 A1 | 6/2012 | Serowski |
| 2016/0030031 A1 | 2/2016 | Vogtherr |
| 2021/0128269 A1 | 5/2021 | Vipperman et al. |

\* cited by examiner

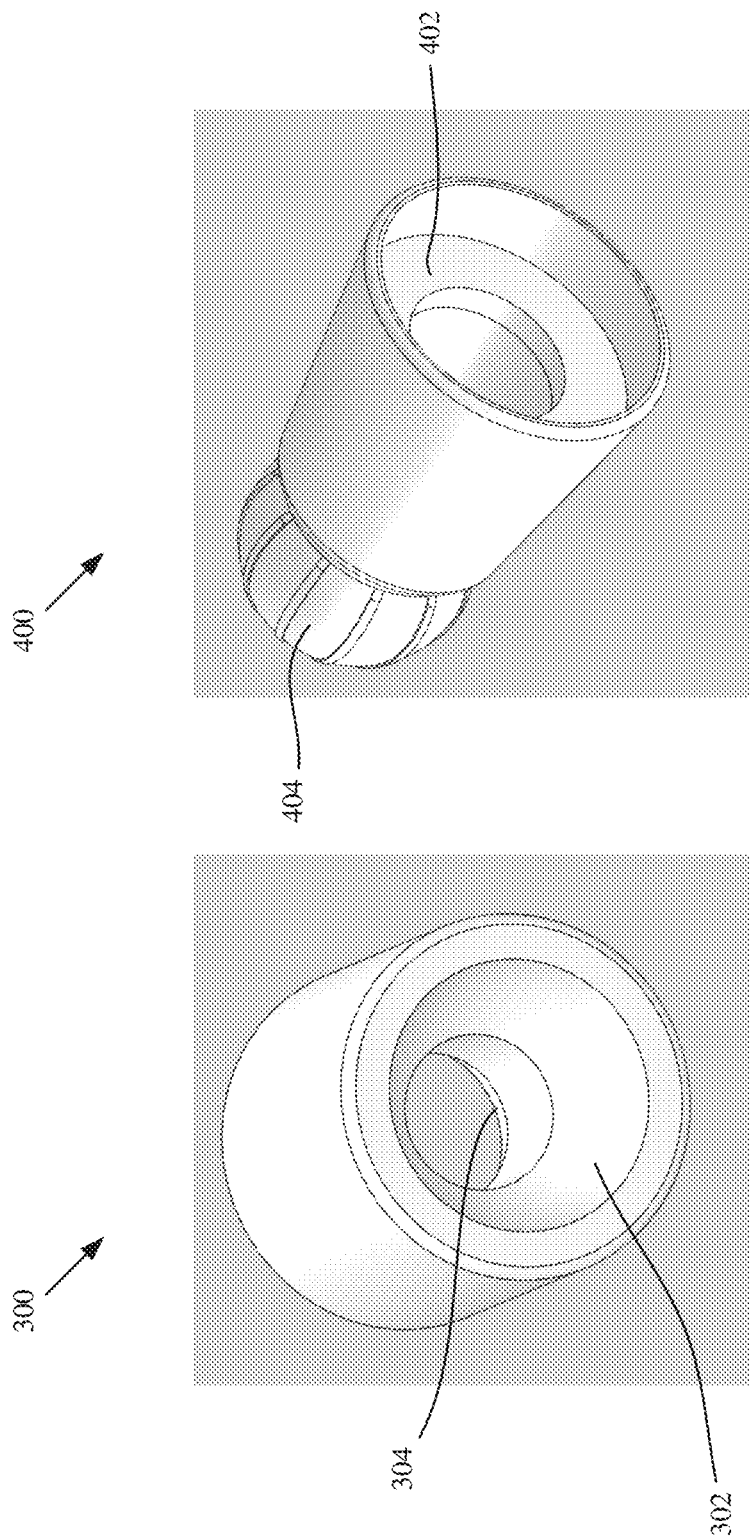

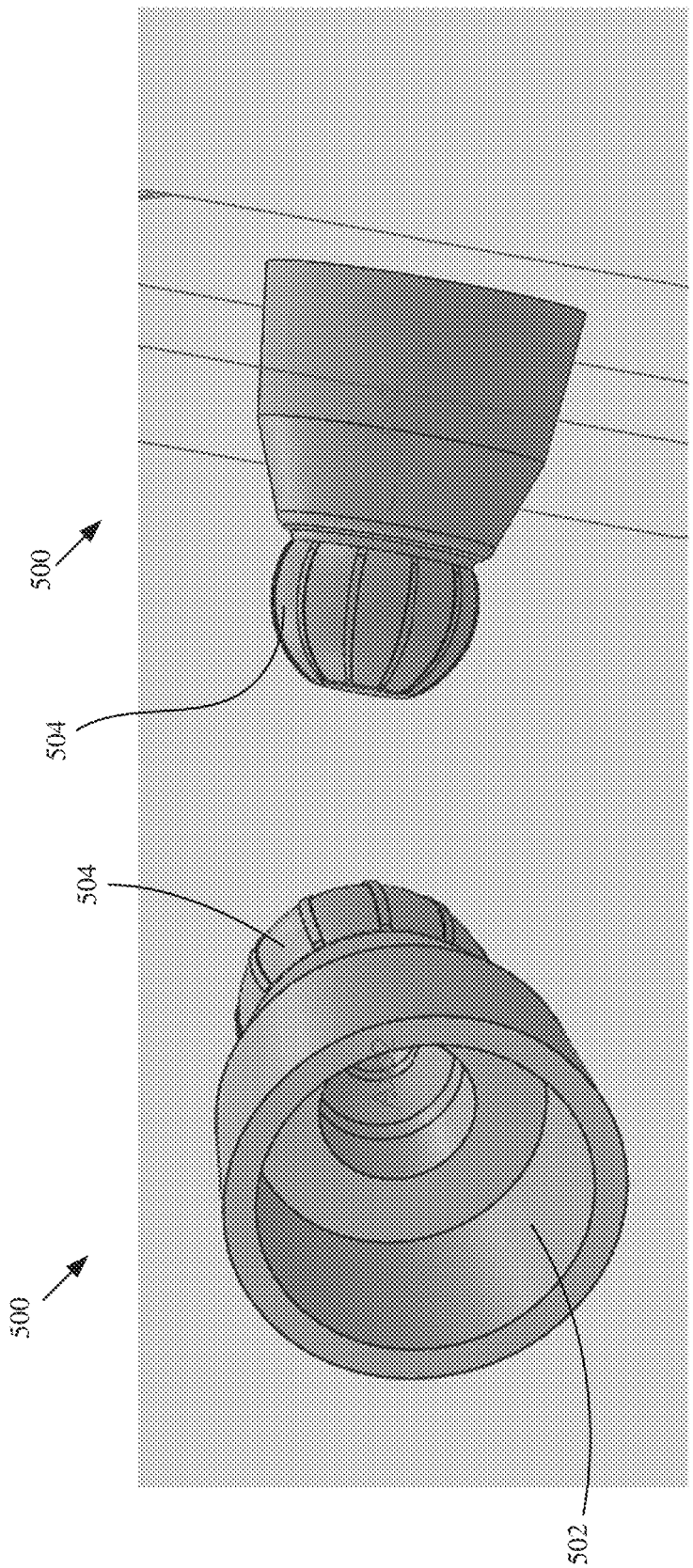

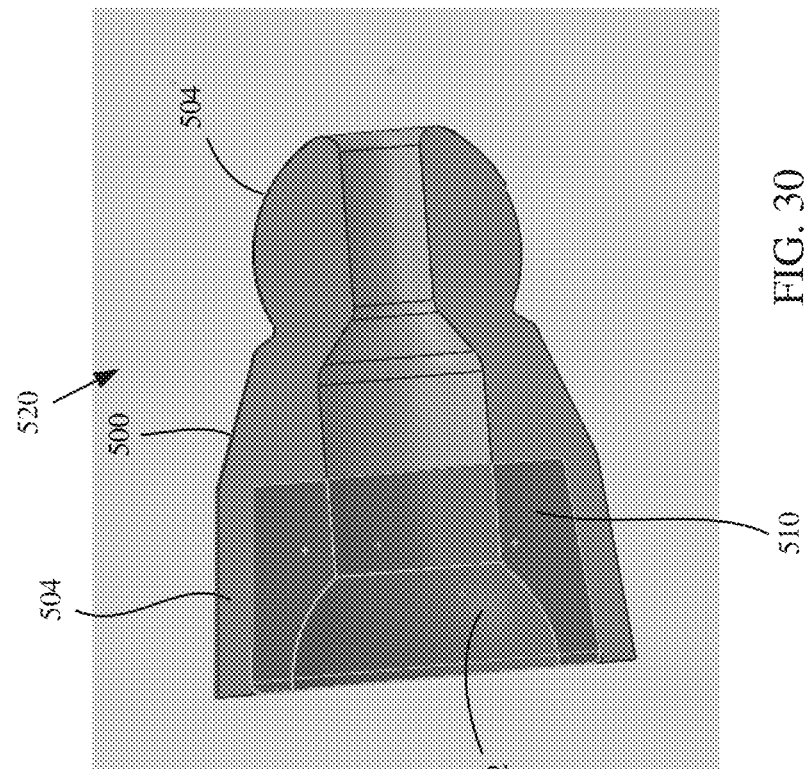
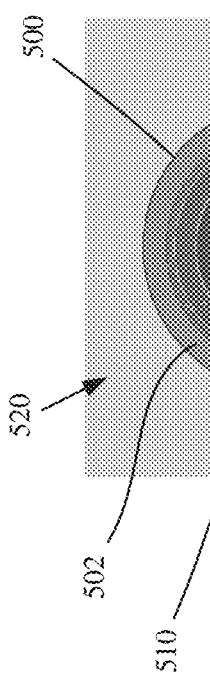
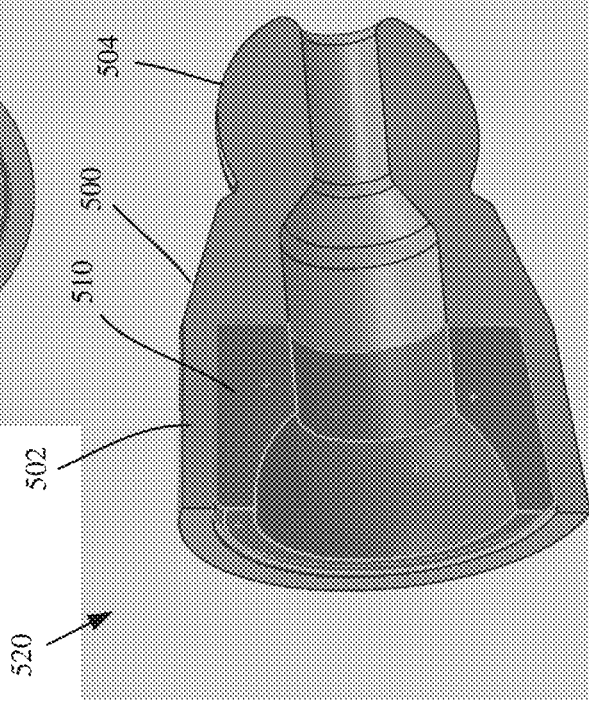
FIG. 31
FIG. 29
FIG. 30

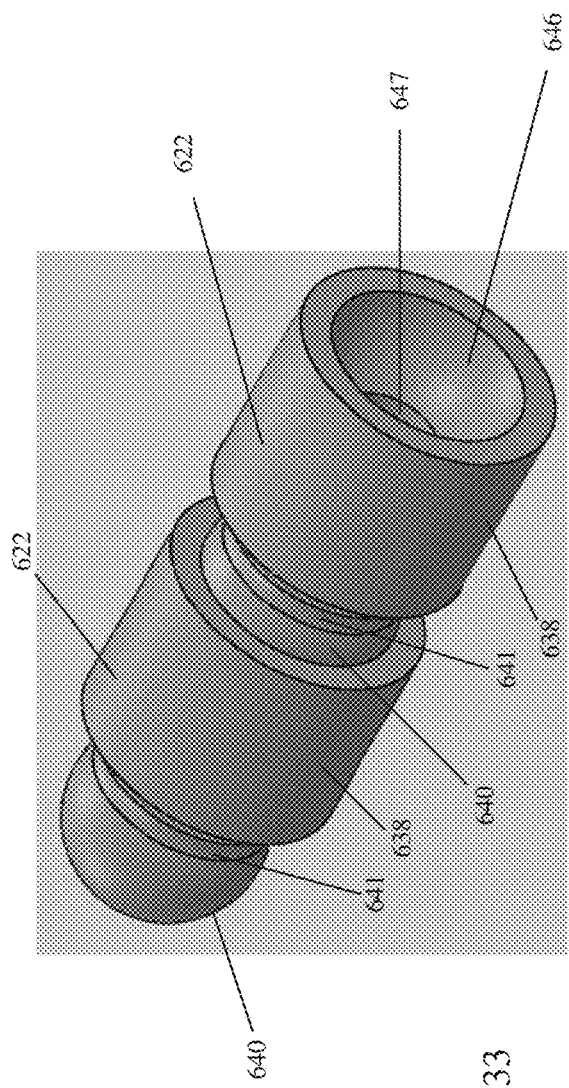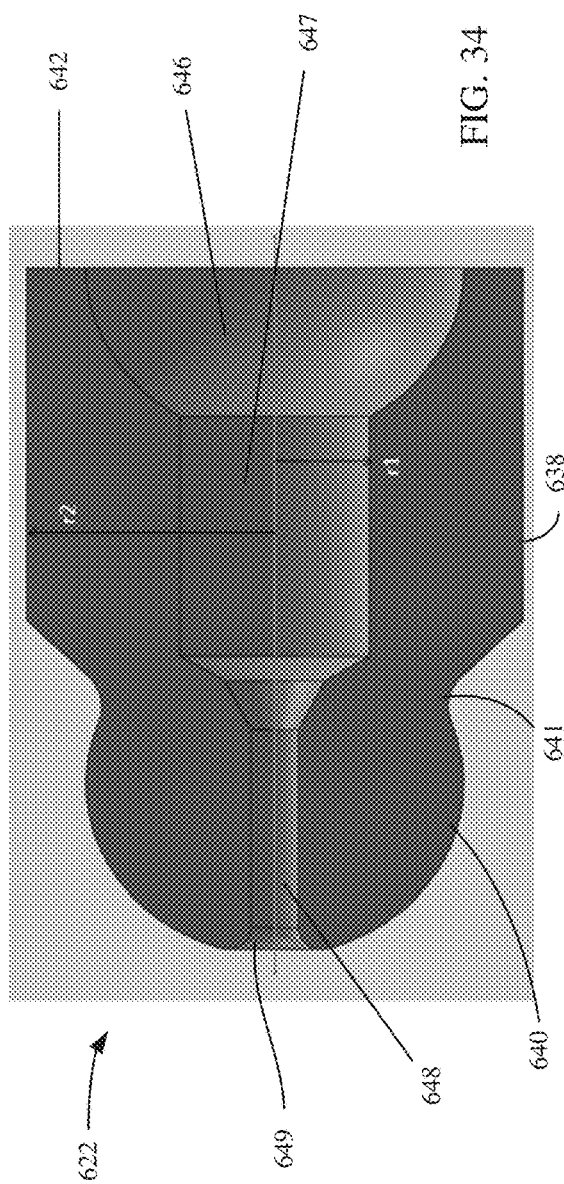

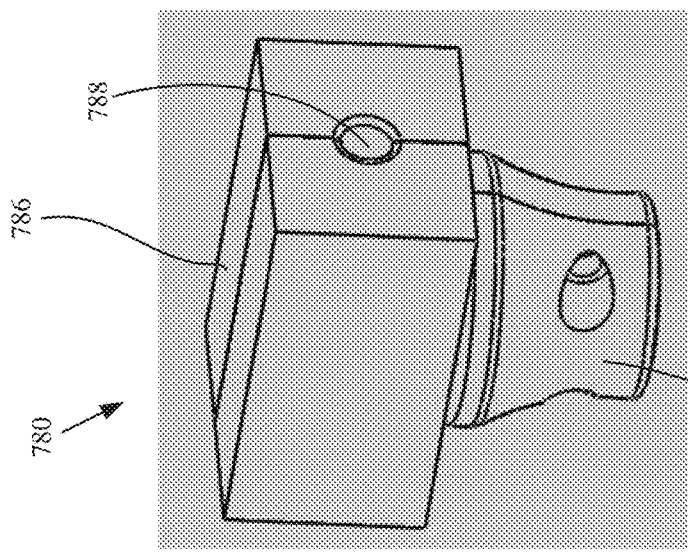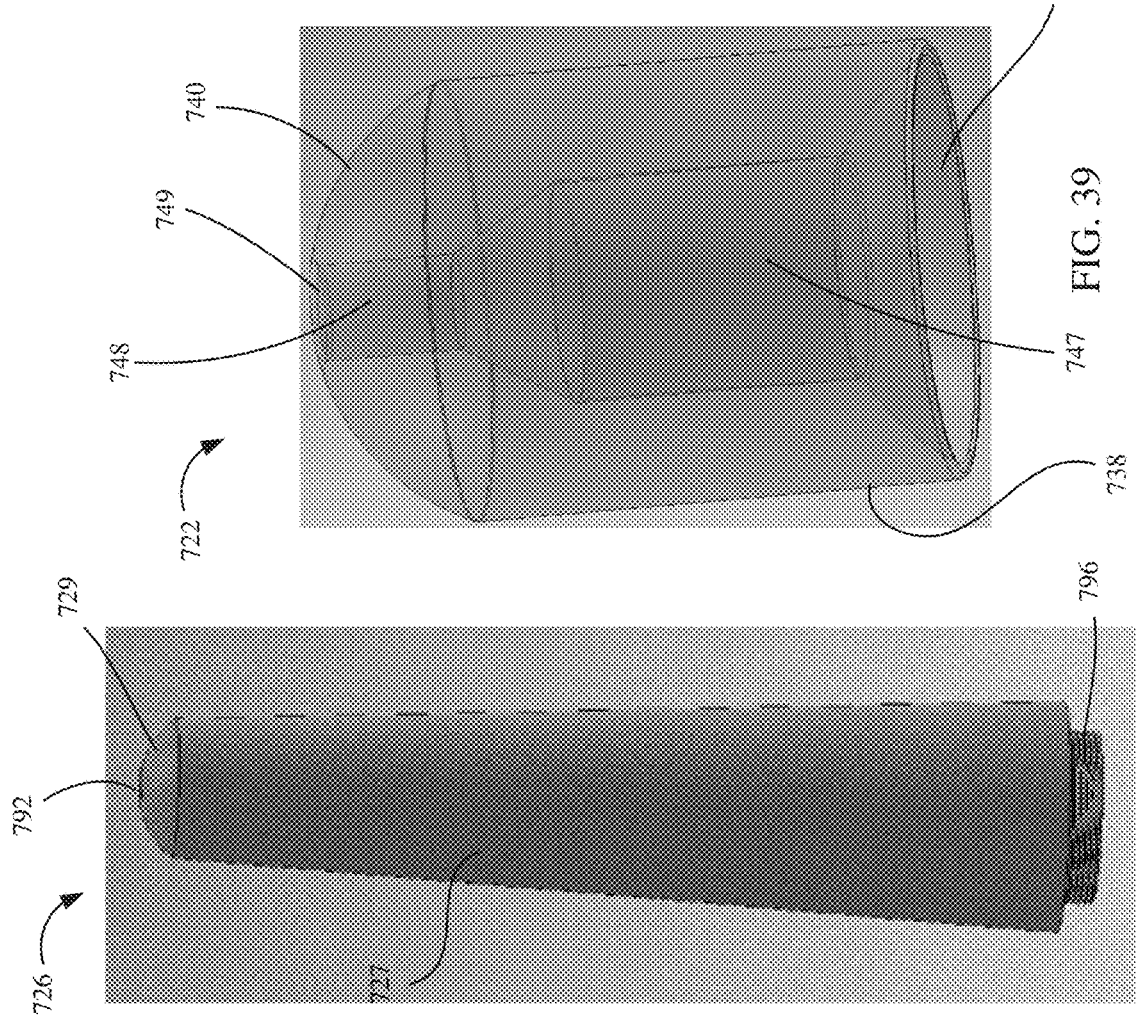
FIG. 40
FIG. 39
FIG. 38

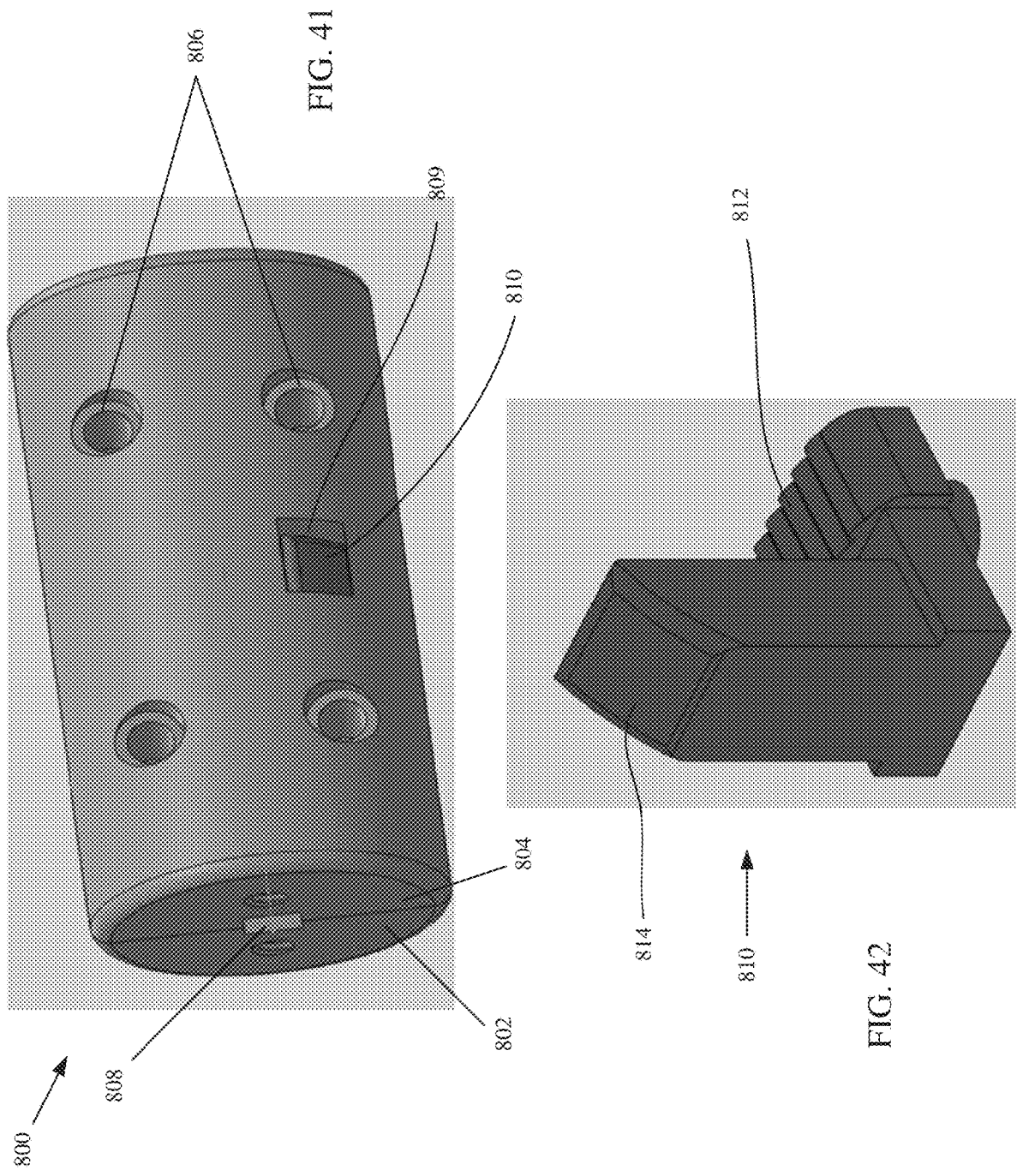

| Case | Mode | V1 | V2 | V3 | V4 |
|---|---|---|---|---|---|
| | | | Valve Truth Table | | |
| Case 1 | Off | Open | Closed | Closed | Open |
| Case 2 | Load | Open | Closed | Open | Closed |
| Case 3 | Run | Closed | Open | Closed | Open |
| Case 4 | Button Press, Load | Open | Closed | Open | Closed |

FIG. 47

ADJUSTABLE RETAINING ARM SYSTEM

CROSS-REFERENCE TO RELATED APPLICATIONS

This application is a continuation of U.S. patent application Ser. No. 16/480,926 filed Jul. 25, 2019, which is the U.S. National Stage of International Application No. PCT/US2018/016594 filed Feb. 2, 2018, and claims the benefit of U.S. Provisional Application No. 62/453,608 filed Feb. 2, 2017, all of which are herein incorporated by reference in their entirety.

STATEMENT OF GOVERNMENT SUPPORT

This invention was made with government support under grant #MMI1130289 awarded by the National Science Foundation. The government has certain rights in the invention.

FIELD

The present disclosure concerns adjustable retaining arms and related systems for use during surgical procedures, for example to hold retractors, clamps, or other devices in desired positions during surgical procedures, and for use in various other industries outside of surgery.

BACKGROUND

The open abdomen presents several surgical challenges due to its inherent anatomic complexity, the depth of the surgical field, and the technical difficulties exacerbated by the epidemic of morbid obesity. Open abdominal procedures include operations that utilize an incision that violates the peritoneum (the lining of the abdominal cavity) allowing for direct visualization and manual manipulation of the abdominal or pelvic contents. The incision most frequently used in open abdominal surgery is called a laparotomy, which is a comparatively large vertical incision in the midline of the abdomen. The edges of the skin and appropriate organs and tissues are retracted to allow for visualization and manipulation of the target tissue. There are multiple methods of surgical retraction, but a majority of procedures follow a similar pattern. Initially during the procedure, manual retractors are held by the surgeon or assistants creating single-point or two-point retraction to visualize the target. Frequently thereafter, a more formidable hands-free retractor is used, one which can be set up to hold multipoint retraction without using additional hands or assistants. This is sometimes referred to as the "natural progression" of retraction in the open abdomen.

The Bookwalter retractor is an example of a conventional multi-point, hands-free retraction device that is called for by a majority of surgeons when opening the abdomen using a laparotomy incision. Little has changed since its initial design decades ago. This device uses a steel ring which is held over the abdominal incision by one or two perpendicular metal posts attached to the operating table. Different retractor blades are attached to the ring, which pull the incision open, allowing for exposure. Many similar devices exist following the same concept of forming or fixing a metal ring around the abdomen to hold the incision open. The purpose is to allow for maximal exposure and to keep the surgeon's and assistant's hands free to operate.

The Bookwalter retractor and other retractors solve the basic problem of exposure, but do so at the expense of speed, comfort, adjustability, and convenience. These retractors take much time to set up, creating an "intermission" in the operation. They can be difficult to align properly and even mild adjustments can become complex. Furthermore, the attachment point of these bulky retractors to the rail of the operating table, as well as operating through a metal ring, can make the surgeon uncomfortable or create difficulties with positioning for assistants. Still further, the surgeon is constrained to retract from the limitation of a large metal ring hanging over the outside of the abdominal cavity. If retraction is required deep within the abdominal cavity where the attachable retractor heads cannot reach or at an angle that is not in the direction of the ring, then the surgeon must readjust or return to standard manual retraction. The ring can also interfere with the path of overhead surgical lighting, casting shadows on tissues within the body and requiring an assistant to provide lighting manually.

Frequently, in under-staffed settings, such as in community hospitals without 24/7 resident coverage, the surgeon may find that an assistant is unavailable, such as when operating on emergencies or any non-scheduled operations, such as those at night. In such cases, the surgeon may have to operate with a scrub technician performing the normal duties of both the assistant and the technician. This can make performing emergent surgeries quite difficult, and the use of a hands-free retractor can become a necessity even though it will take significantly longer to set up a Bookwalter retractor without a dedicated assistant.

In the fields of laparoscopic and thoracoscopic surgery, for example, additional equipment can also be needed to retain imaging, lighting, and other specialized surgical devices, which places an additional demand on the hands of the available medical professionals.

As a further example, the field of trauma surgery can provide an additional requirement for retraction due to substantial bleeding. For example, during emergent laparotomies for unstable trauma, there is frequently a large amount of blood in the surgical field that increases the difficulty of the operation. The exact source of the bleeding can be unknown, and thus fast and efficient retraction can be vital. Accordingly, retractor systems including the Bookwalter and other retractor systems can be essentially unusable until after a patient is stable due to prolonged set up time and complex adjustments. As a result, manual retraction is almost exclusively utilized in practice until bleeding is controlled and the patient stabilizes.

SUMMARY

Disclosed herein are adjustable retaining arm systems that can be used in various applications, such as in surgical or other medical procedures, for example during abdominal or thoracic open surgery or minimally invasive (laparoscopic or thoracoscopic) surgery. The disclosed systems include an adjustable retaining arm comprising an elongated, multi-segmented, articulated column having a proximal end that can be fixed in relation to the operating table or other support structure, and a distal end that is positionable in a customizable orientation adjacent to the surgical zone and holding one or more surgical tools such as a retractor tool in a desired position relative to a surgical site in a patient.

The system is configured such that the arm in a relaxed state can be adjusted into a desired configuration by manually articulating the arm at joints between the arm's segments, and the arm can be made rigid and fixed in a desired configuration by applying compression along the arm using a tension cable running through the length of the arm.

Tension can be applied to the cable using a tensioning system located in a support structure, e.g., a box mounted on the side of the operating table. Tension in the cable compresses all the arm segments together longitudinally and creates sufficiently high friction, interlocking, or other interference between adjacent arm segments, inhibiting the segments from articulating relative to each other. The arm tensioning system can be controlled based on any type of user input (such as pressing a foot pedal, pressing a hand-actuated button on the mounting box or near the distal end of the arm, via voice commands, other wireless or remote input device, etc.). For example, the arm can be made flexible by one user input, set to a desired shape, then made rigid by another user input. This control system allows for rapid adjustment and re-adjustment of the arm's location and shape before and during surgery. In various embodiments, one or more retractor tools, clamps, lights, or other tools are coupled to the distal end and/or intermediate parts of the arm. For example, multiple retractors mounted along the arm can be used to retract on tissue at multiple points in various directions, such as in a circular or semicircular fashion around an open incision. The arm is easily adjustable allowing for the natural progression in surgery of using one retractor or other tool and transitioning to multiple tools without interruption.

In some embodiments, an adjustable surgical retaining arm comprises plural rigid arm segments arranged end-to-end along a longitudinal axis of the arm and forming articulation joints between adjacent axial ends of the arm segments, wherein the arm segments include axial passageways extending through the arm segments. The arm further comprises a cable extending through the axial passageways of the arm segments and a proximal mounting platform coupled to a proximal end of the arm segments, with the cable extending through the mounting platform, such that the mounting platform is configured to attach and detach a proximal end of the arm to and from a rigid support structure that is fixed relative to a surgical table or other nearby support structure, and is configured to couple and decouple a proximal end of the cable to and from a cable tensioning device. The arm has at least one adjustable state when tension in the cable is less than an operative tension, wherein in the adjustable state the arm can be arranged in a desired position by articulation at the joints between the arm segments such that the surgical tool can be placed in a desired position relative to a surgical patient, and the arm has a rigid state when tension in the cable is at least the operative tension. The arm also has at least one rigid state wherein the tension in the cable applies axial compression along the arm and creates frictional resistance and/or mechanical interlocking in the joints between the arm segments that is sufficient to restrict the arm from articulating and holds the surgical tool in the desired position.

In some embodiments, the system can further comprise a rigid mounting structure (e.g., a box or enclosure mountable to the operating table), a cable tensioning system supported by the rigid support structure (comprising a receiver that engages a proximal end of the cable, an actuator that applies tension on the cable, and optionally a tension sensor that measures the amount of tension applied to the cable), a user input device, optionally a gas regulator, and control system. The control system can receive user input signals from the user input device and receive signals from the tension sensor indicating the measured amount of tension applied to the cable, and based on the user input signals and the measured amount of tension the control system the control system can change the arm between at least one adjustable state and at least one rigid state by adjusting the amount of tension that is applied to the cable by the actuator.

In some embodiments, the arm segments each include a convex head at one end and a concave recess at an opposite end, and the heads of the segments articulate within the recesses of adjacent segments. The convex heads can comprise spherical or ball shaped heads and the concave recesses comprise correspondingly shaped spherical or conical or tapered sockets. The segments can include passages extending from the recesses through the heads to allow passage of the cable through the segments. In some embodiments, the articulation surfaces between the arm segments can include roughened areas, ridges, grooves, or other rigidity enhancing features to increase strength when the arm is in the rigid state. The arm segments can also include interlocking features at the joints between the arm segments such that the interlocking features mechanically engage when the arm is in the rigid state and restrict the joints from articulating. The arm segments and other arm components can be made from any of various strong, light-weight materials that provide sufficient friction/rigidity when under compression, such as certain metals/alloys and injection moldable polymeric or composite materials.

The foregoing and many other features and advantages of the disclosed technology will become more apparent from the following detailed description, which proceeds with reference to the accompanying figures.

BRIEF DESCRIPTION OF THE DRAWINGS

FIG. 23 shows an exemplary double concave arm segment.

FIG. 24 shows an exemplary arm segment with a cavity at one end for receiving an insert.

FIGS. 25 and 26 shows another exemplary arm segment with a cavity at one end for receiving an insert.

FIGS. 29 and 30 are cross-sectional views of the arm segment of FIGS. 25 and 26 combined with the insert of FIGS. 27 and 28.

FIG. 31 is an end view of the arm segment of FIGS. 25 and 26 combined with the insert of FIGS. 27 and 28.

FIG. 33 shows two segments of the arm system of FIG. 32.

FIG. 34 is a cross sectional view of a segment of FIG. 33.

FIG. 38 shows an elongated proximal segment of the arm of FIG. 36.

FIG. 39 shows an intermediate segment of the arm of FIG. 36.

FIG. 40 shows a tool attachment adapter that is included in the arm of FIG. 37.

FIG. 41 shows an exemplary tool adapter that couples to a distal end of a retaining arm, including a ratcheting mechanism for attaching a tool.

FIG. 42 shows a ratcheting component of the adapter of FIG. 41.

FIG. 47 is an exemplar solenoid valve/actuator truth table.

DETAILED DESCRIPTION

Figure 1:
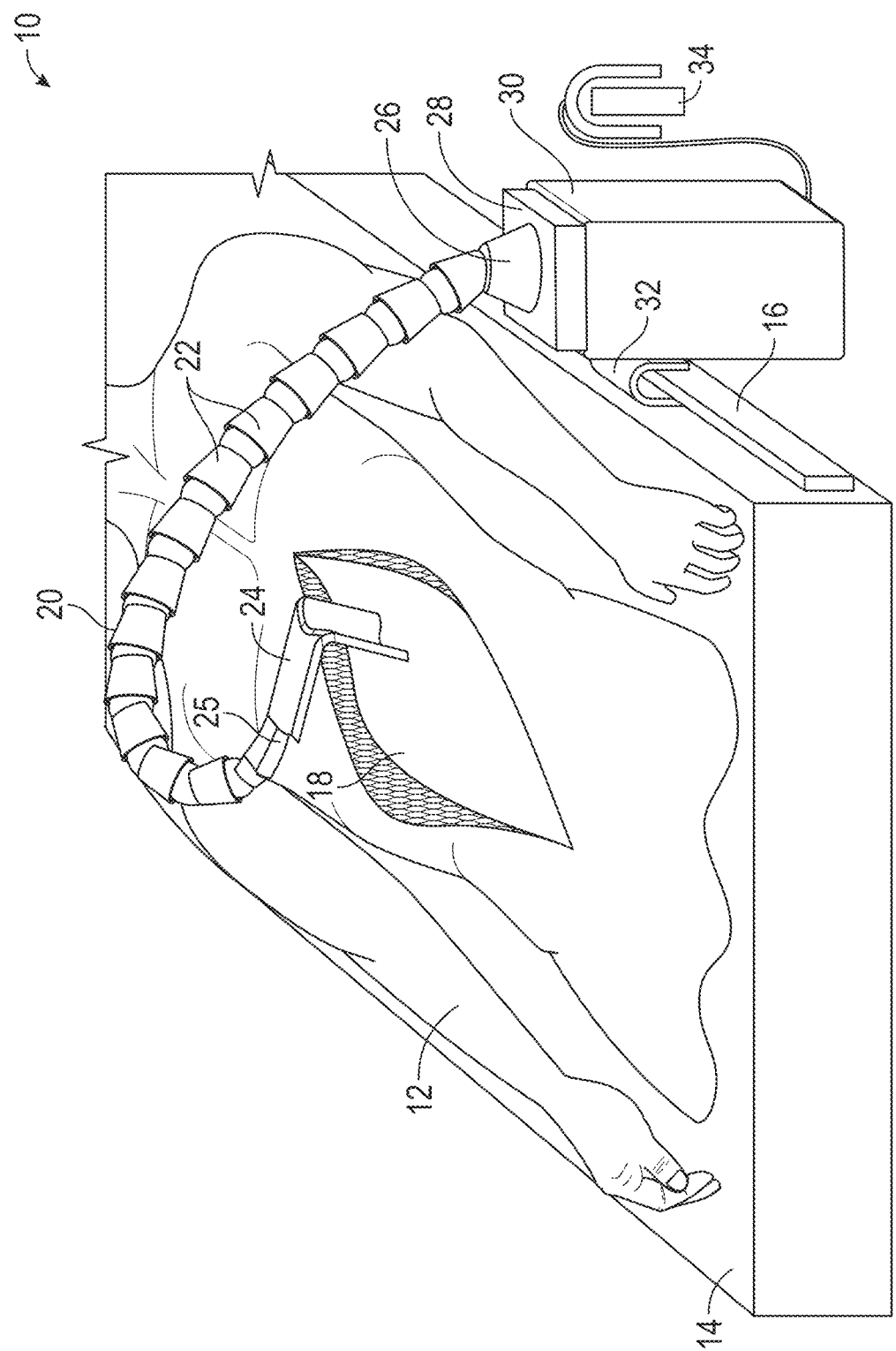
FIG. 1 shows an exemplary adjustable retaining arm system in use with an abdominal surgery patient.

FIG. 1 shows an exemplary environment including an exemplary arm system 10 illustrating the technology disclosed herein. The system 10 can comprise an adjustable arm 20, a box 30 including actuation and control components, and a foot pedal 34 (or other user input such as a button on the box 30 or on the arm 20). The box 30 can comprise any shape, size, or structure, and does not need to be rectangular or fully enclosed. The box 30 can be located anywhere on or around the surgical table, and can be attached to the table or supported otherwise apart from the table. The box 30 can comprise two or more units in some embodiments, such as one unit to support the arm 20 and an actuator that applies tension on the arm 20, and one or more additional units that include control components, computing or logic components, power supply components, etc. As shown in FIG. 1, the box 30 can be coupled to a side rail 16 of a surgical table 14 in a manner that holds the box and the proximal end of the arm 20 in a fixed position relative to a surgical patient 12, while the distal end of the arm is suspended over the patient 12.

As used herein, the term "proximal" refers to a position, direction, or portion of a device that is closer to the location where the arm is coupled to its support structure or other anchor point and further away from the end of the arm that is adjacent the surgical location in the patient. As used herein, the term "distal" refers to a position, direction, or portion of a device that is further away from the location where the arm is attached to the support structure or other anchor point and closer to the end of the arm that is adjacent the surgical location in the patient. The terms "longitudinal" and "axial" refer to an axis extending in the proximal and distal directions, unless otherwise expressly defined. The term "radial" refers to directions extending perpendicularly away from the longitudinal axis. The term "circumferential" refers to directions extending around the longitudinal axis.

The arm 20 can have any length suitable for the particular parameters of the surgery, patient, table, etc. The length of the arm can be selected based on the type of table, type of patient, type of surgery, type of surgical tools being used, and/or other factors. In some embodiments, the arm 20 has an overall length (including the mounting platform and distal tool adaptor) of at least 25 cm, at least 50 cm, at least 75 cm, at least 100 cm, at least 125 cm, at least 150 cm, at least 175 cm, and/or at least 200 cm. In some embodiments, the arm 20 has an overall length from about 25 cm to about 200 cm, from about 50 cm to about 175 cm, and/or from about 100 cm to about 150 cm.

Figure 2:
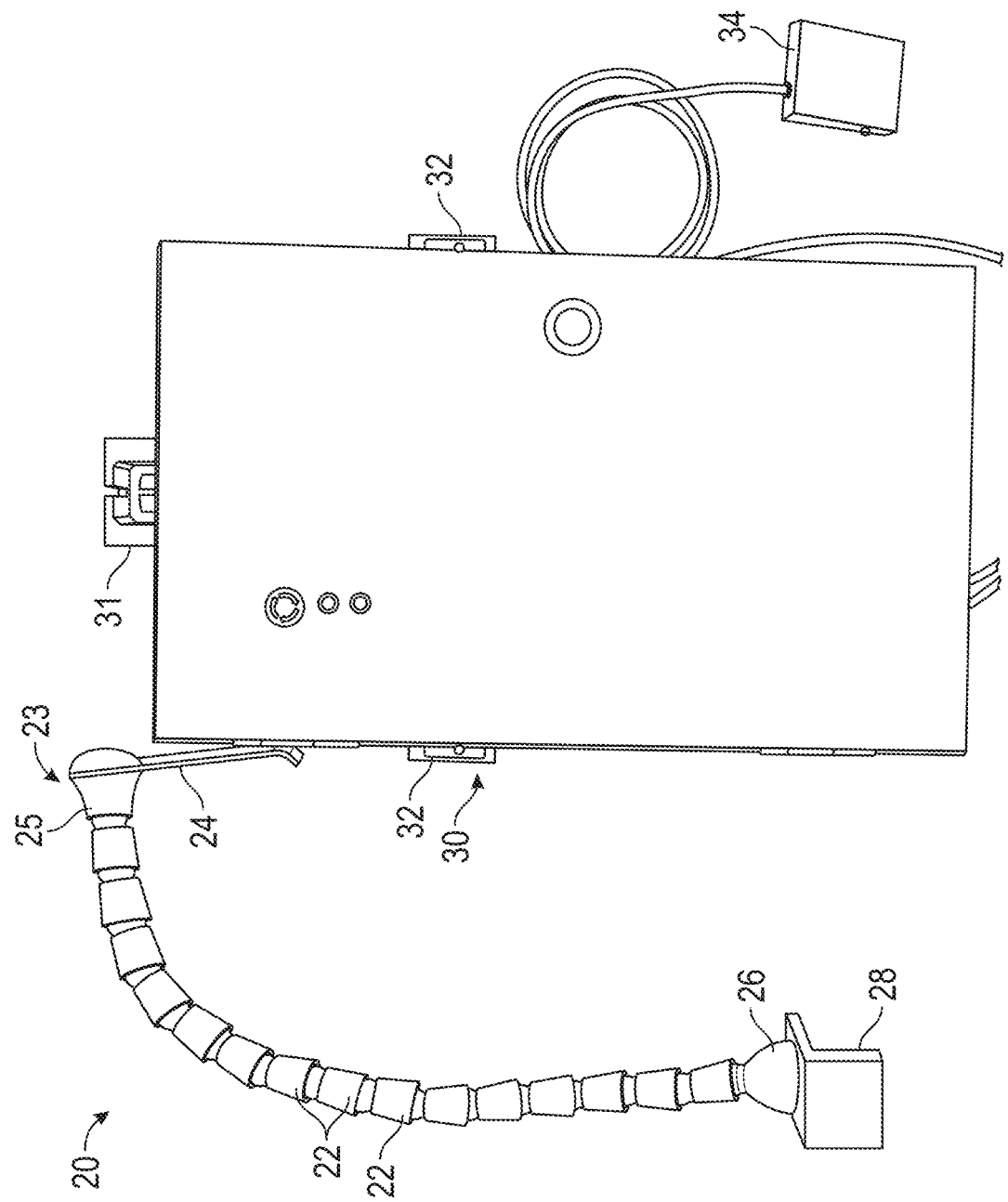
FIG. 2 shows components of the system of FIG. 1, including an adjustable arm component, an actuation and control unit (contained in a box), and a foot pedal actuator.
Figure 3:
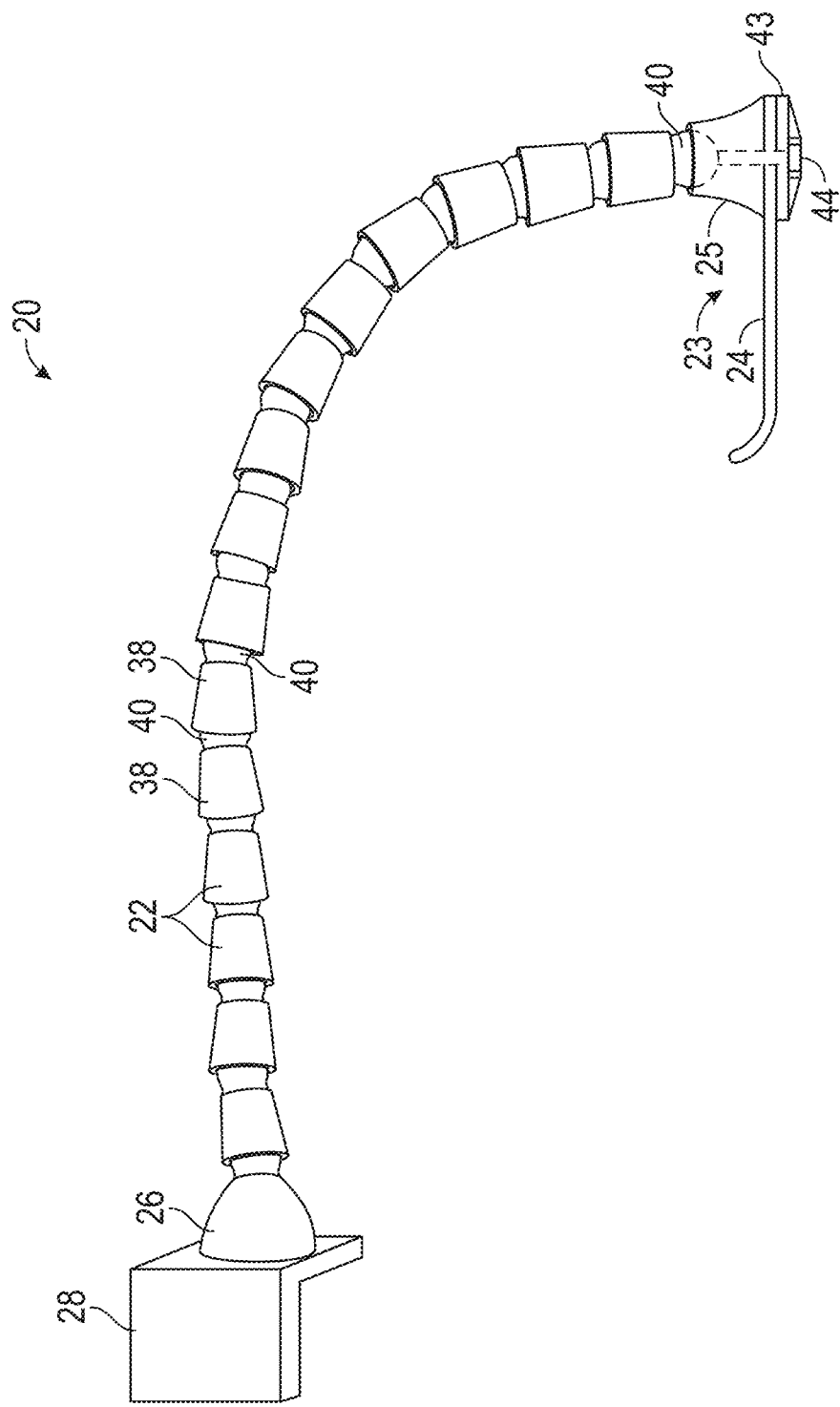
FIG. 3 is an enlarged view of the adjustable arm component.
Figure 9:
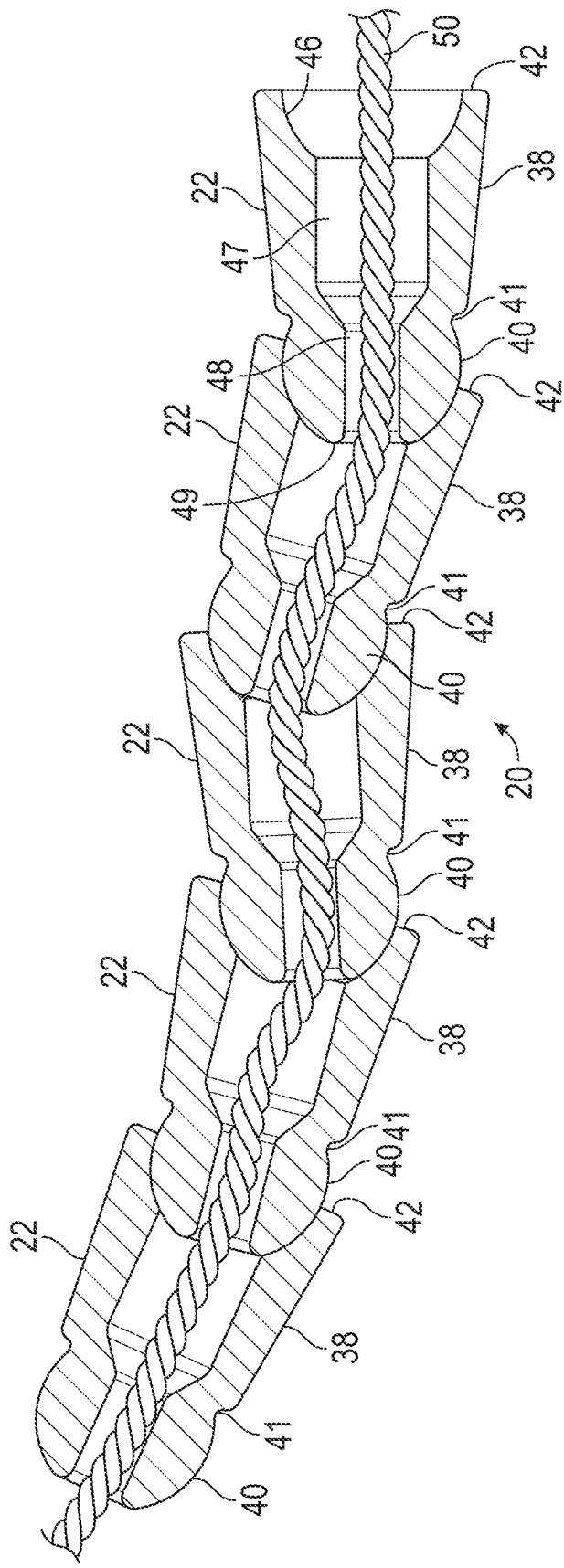
FIG. 9 is a cross-sectional view of a portion of an exemplary adjustable retaining arm comprising several hollow arm segments that are articulable relative to each other, and with a tension cord running through the openings of the segments.

As shown in FIGS. 2, 3 and 9, the arm 20 comprises a plurality of segments 22 that articulate relative to each other, with a tensioning cable 50 running through central passages in the segments and coupled to a tensioning device inside the box 30. The segments 22 can be any length and diameter suitable for a particular application. Greater diameters can provide increased arm strength in the rigid state, and can allow the arm to handle greater compressive loads applied by the tension cable. The arm can include any number of the segments 22, such as at least one segment, at least two segments, at least five segments, at least ten segments, etc. More or fewer segments, or shorter or longer segments, can be included in the arm to adjust the length of the arm. In some embodiments, segments can be added to increase the arm length or segments can be removed to decrease the arm length.

The components of the arm, including the segments 22, a proximal adapter 26, and a distal tool adapter 25, can comprise any of a variety of suitable materials, including metals, polymeric materials, and/or composite materials that are suitable strong and can provide a sufficient degree of rigidity. A distal end of the arm 20 can include a tool adapter 25 that allows for the attachment of selected surgical tools, such as retractor heads (an exemplary retractor head 24 is illustrated in FIGS. 1-3). The segments 22 can also be configured so that the intermediate portions of the arm 20 can also be used to mount retractor heads, or other tools, such as to provide multiple points of retraction (see FIG. 7 for example).

Figure 7:
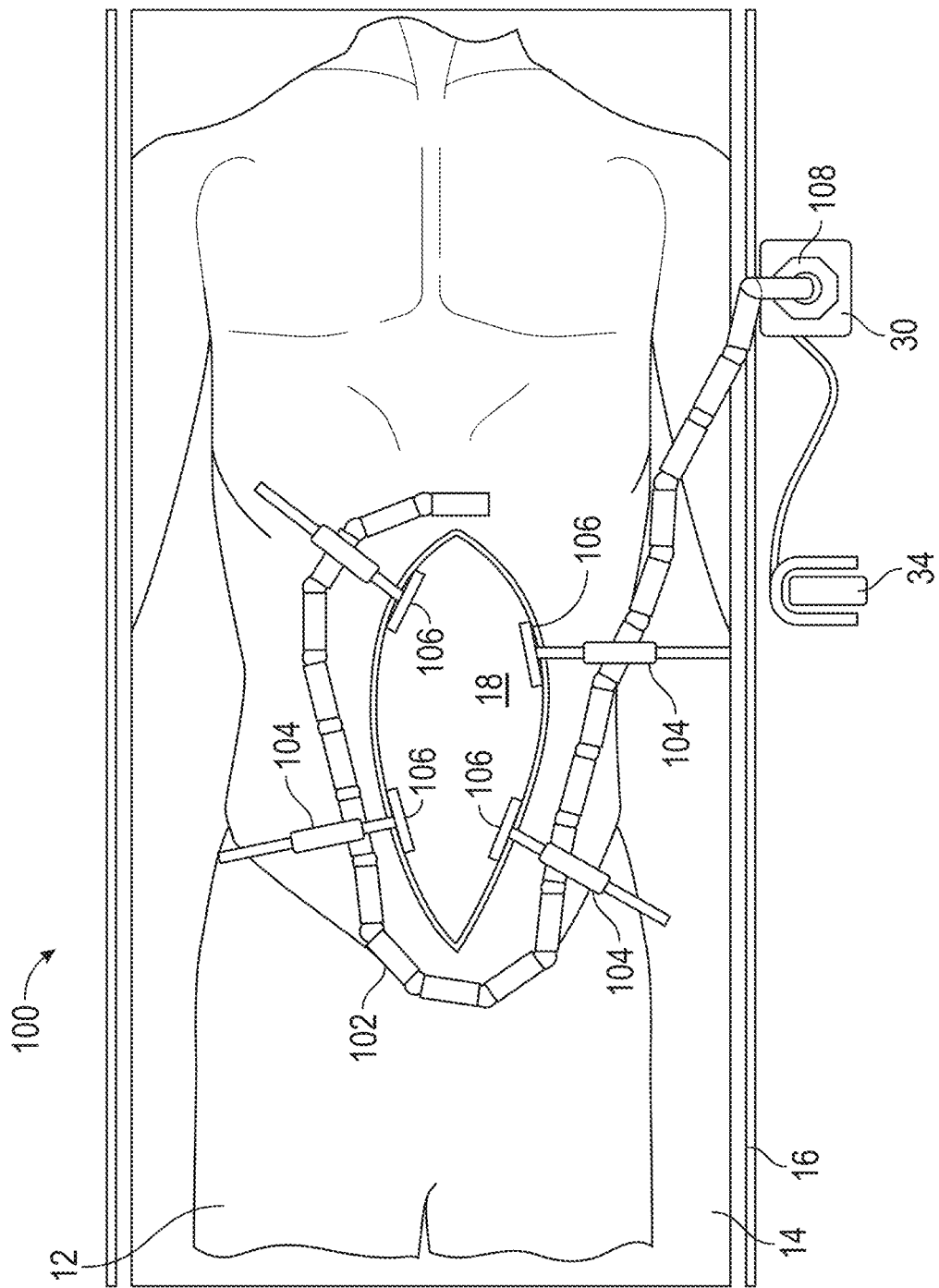
FIG. 7 is a top-down view of a surgical patient on an operating table with another exemplary adjustable retaining arm system positioned to hold four surgical retractors in desired positions around a surgical opening in the patient.

FIG. 7 shows a system 100 that includes an arm 102 comprising four different retractor tools 104 mounted at various points along the length of the arm. Each tool 104 is able to apply retraction in the surgical area 18 via independent retractor heads 106. The base 108 of the arm 102 is mounted to the box 30 and the arm can be articulated around the surgical opening as desired to place the retractor tools 104 at any position and any orientation desired. Though four retractor tools 104 are shown, any number of various kinds of surgical tools can be attached to arm 102 at any point along its length. When compression is applied to the arm via the inner cable, the arm becomes rigid, holding the tools in place.

Figure 6:
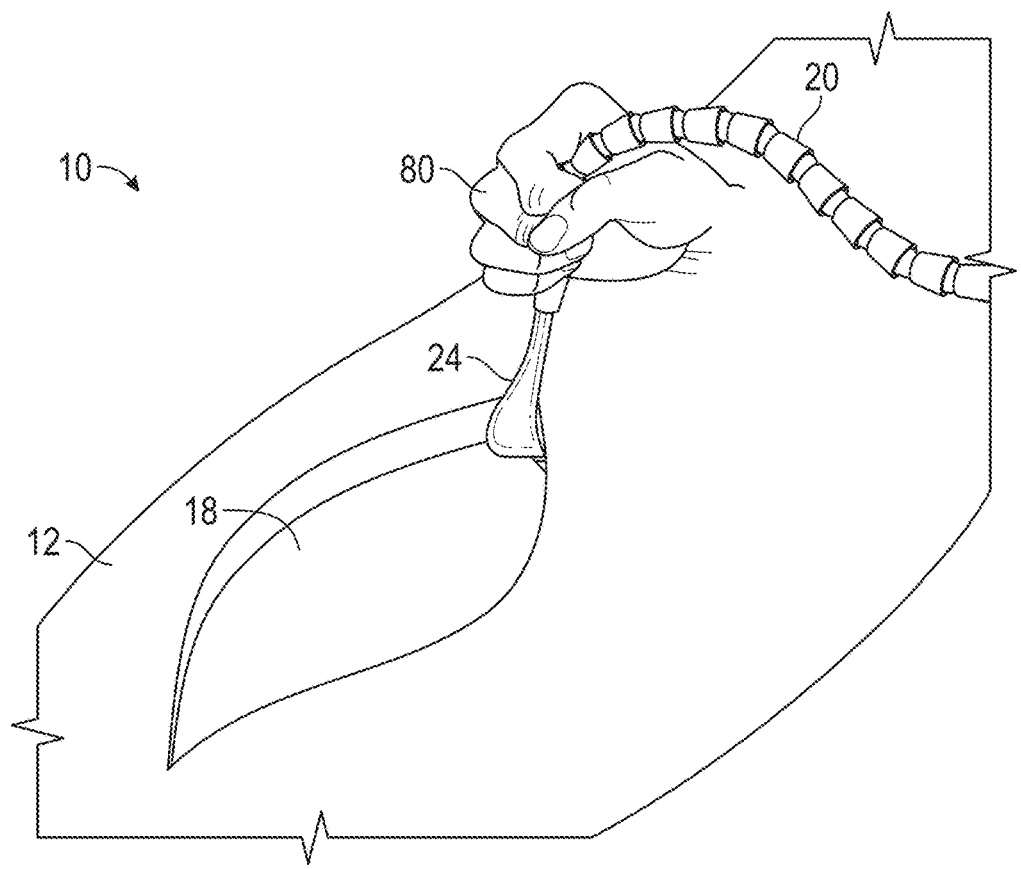
FIG. 6 illustrates a distal end of the arm component with a surgical retractor attached being manually positioned relative to a surgical opening in a patient.
Figure 8:
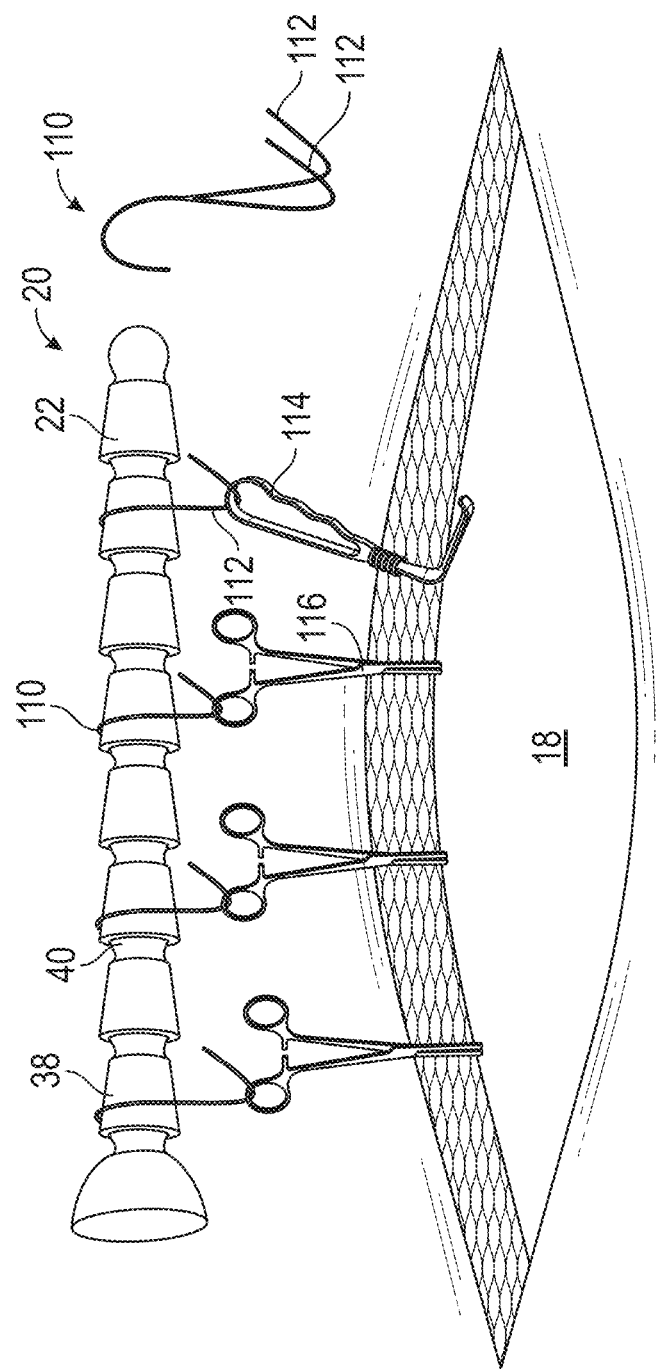
FIG. 8 shows a portion of an adjustable retaining arm with several surgical tools coupled to the arm.

FIG. 8 illustrates how retainers, such as the exemplary retainer 110, can be used to couple tools to the several segments 22 of the arm. The example retainer 110 includes hooks 112 to engage tools such as clamps 116 and retractors 114. The retainer 110 can mount around any part of the arm 20/102 and be sufficiently rigid to transfer forces between the arm and tools. The segments 22 of the arm can optionally include grooves, notches, openings, or other features to receive and hold the retainers 110. The retainers 110 can be readily removed and placed at desired positions along the arm. For example, after a distal tool is initially placed (for example see FIG. 6), additional tools can be added one at a time to intermediate locations along the arm using the retainers 110. In other embodiments, tools can be mounted or attached directly to the arm without the retainers.

FIG. 9 is a cross-sectional view of an intermediate portion of the arm 20 including five of the segments 22 and the cable 50 running through the middle of the segments. Each segment 22 can include a base 38 and a head 40. Each head 40 is inserted into a correspondingly shaped recess 46 in the base of the adjacent segment. The recess 46 can be spherical, conical, or otherwise shaped to receive the head 40. The recess 46 does not need to have an exact shape corresponding the same curvature as the head 40. However, some degree of tapering or angularity may be desirable in the recess 46.

Figure 10:
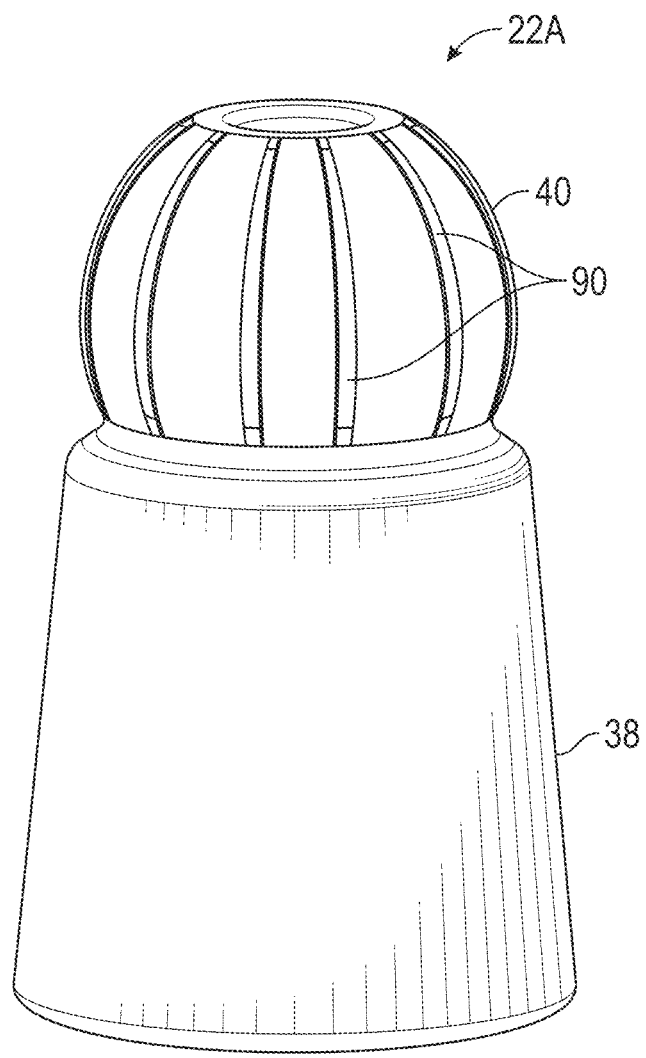
FIG. 10 is a perspective view of a single arm segment that has grooves in its rounded head portion to provide mechanical interlocking and/or friction enhancement in the joints.

The heads 40 and or the recesses 46 can optionally include friction enhancing and/or mechanically interlocking/interfering surface features. FIG. 10 shows one exemplary segment 22A that includes longitudinal ridges 90 on its head 40. Such feature can provide for enhanced friction and/or provide mechanical interlocking when the arm is under compression. Longitudinally extending features, like the ridges 90, can help resist relative rotation/twisting between the adjacent segments, while horizontally extending features (latitudinal features) can help resist pivoting between adjacent segments. The recesses 46 can optionally include similar and corresponding features. In other embodiments, the heads 40 and/or the recesses 46 can have a smooth surface or any other type of roughness, ridges, grooves, bumps, knurling, and/or other non-smooth features to enhance friction and/or mechanical interlocking/interference.

As shown in FIG. 9, each segment 22 includes a first passageway 47 passing through the base 38 and a second passageway 48 passing through the head 40, and the cable 50 extends through both passageways 47 and 48 of each segment. The outlet of the second passageway 48 can include a rounded perimeter surface 49 to provide a smoother surface for the cable to contact. When two adjacent segments 22 are fixed at a sharp articulation angle, the cable can bend around the rounded perimeter surface 49 as it changes direction without a sharp edge contacting the cable to reduce any wear, resistance, or damage to the cable or segments. When tension is applied to the cable 50, the cable compresses all of the segments 22 together longitudinally, creating contact forces between the outer surfaces of the heads 40 and the inner surfaces of the recesses 46, which causes corresponding static frictional forces between the segments or mechanical interlocking to prevent or resist the segments from pivoting relative to each other, making the whole arm rigid.

Each segment 22 can include a narrowed neck 41 between its base 38 and head 40, forming a rounded shoulder between the neck 41 and the base 38. The opposite end of the base 38 can have a contact surface 42 that acts as a stop to limit the range of pivoting motion between two adjacent segments. When the pivot limit is reached, the contact surface 42 of one segment contacts the shoulder of the adjacent segment.

In some embodiments, the segments can include coatings or liners at the engagement surfaces to provide desired friction and interference properties at the joints. In some embodiments, the concave recess in the base 38 and/or the convex surface of the heads 40 of the segments can be coated or lined with a material such as rubber, polyurethane, or other polymeric material. In some embodiments, the concave recesses in the bases can receive a washer or insert made of rubber or other polymeric material. Such coatings, liners, washers, inserts, etc., can be selected to provide a specific static coefficient of friction at the joints.

FIGS. 23-29 illustrate alternative segments that can be included in the articulable arms disclosed herein. FIG. 23 shows a double concave segment 300 that include rounded recesses 302 and 304 on both axial ends of the segment. The rounded recesses can engage with a rounded convex head of an adjacent segment or can engage with other rounded convex segments, such as ball-shaped segments similar to the rounded segment 122 shown in FIGS. 19 and 21. In some examples, double concave segments 300 can alternate with double convex segments (e.g., ball shaped segments) along an arm. In some embodiments, the ball-shaped segments can comprise rubber or other similar, harder or softer polymeric materials while the double concave segments can comprise a more rigid material. Materials like rubber can provide enhanced friction between the segments to resist articulation of the joints when the arm is in the rigid state. Compressibility of the rubber material can also allow ridges or similar features on the surface of an adjacent segment to dig into the rubber and create a physical interference that further resists articulation of the joints.

Figures 27, 28:
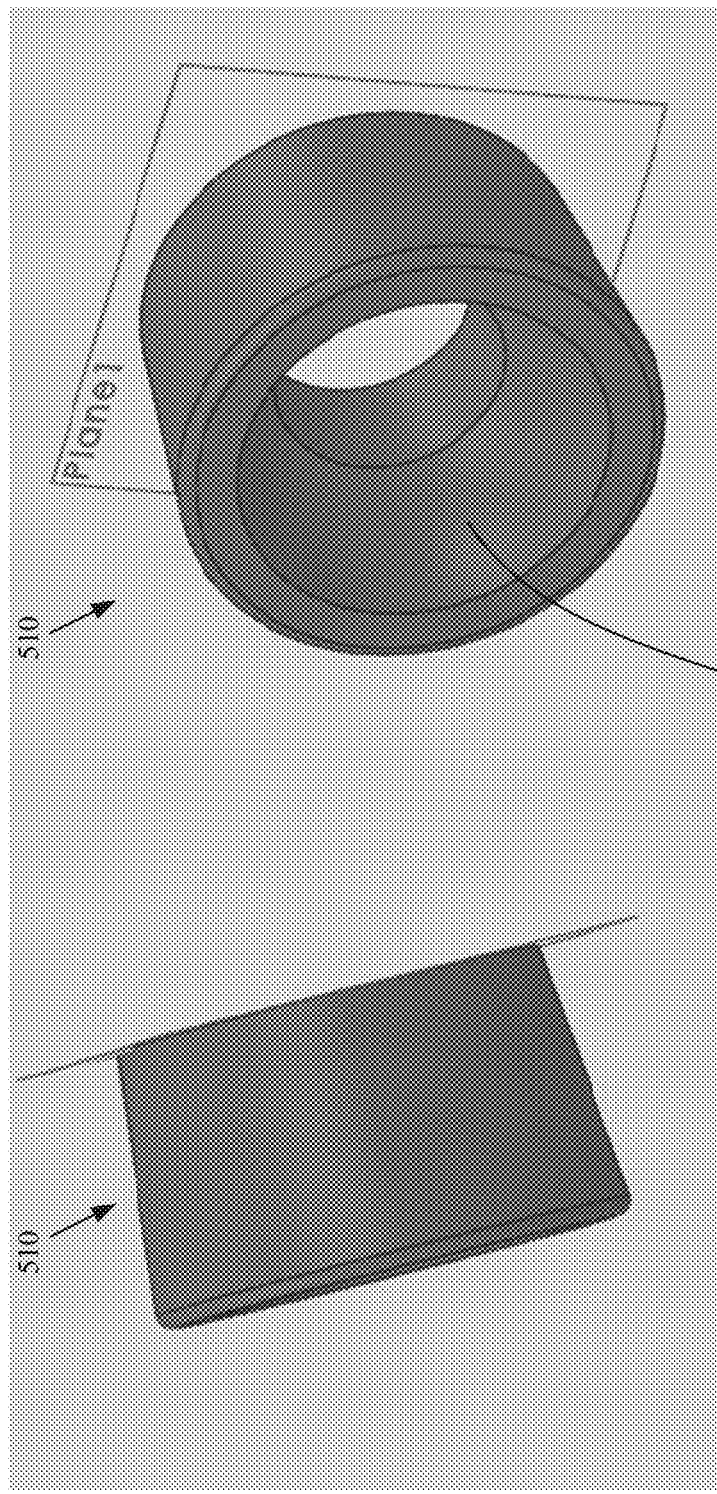
FIGS. 27 and 28 show an exemplary insert that can be used with the arm segment of FIGS. 25 and 26.

FIG. 24 illustrates an exemplary segment 400 that is similar to the segments 22 but has a cavity 402 at one end that is configured to receive insert made of rubber or similar material, such that the insert engages with the convex head 404 of an adjacent segment. FIGS. 25 and 26 illustrate a similar segment 500 that includes a cavity 502 at one axial end for receiving an insert made of rubber or similar material, such that the insert engages with the convex head 504 of an adjacent segment. FIGS. 27 and 28 illustrate an exemplary insert 510 that can be used with the segment 500, as shown in FIGS. 29-31. The insert 510 can comprise rubber or similar material. The insert 510 includes a concave rounded surface 512 that engages with the head 504 of an adjacent segment.

FIG. 3 shows an exemplary embodiment of the arm 20 comprising several segments 22 with a proximal adapter 26 and mounting platform 28 at the proximal end of the arm, and with an exemplary retractor tool 24 attached to the distal tool adapter 25 at the distal end of the arm. In other embodiments, the arm 20 can comprise more or fewer segments 22, and the segments 22 can be longer, shorter, wider or narrower that what is illustrated. In some embodiments, the proximal adapter 26 is not included and the most proximal segment 22 is attached to the mounting platform. In some embodiments, one or more portions of the arm 20 can be permanently rigid and fixed in shape while other parts of the arm comprise articulable segments 22. For example, in some embodiments, a proximal portion of the arm comprises a fixed, rigid tubular body that cannot be adjusted even when the cable is loosened, and a distal portion of the arm comprises segments 22 that form a distal articulable portion of the arm extending from the fixed, rigid proximal portion of the arm. In some embodiments, a proximal rigid portion of the arm extends up from the box 30 to about the level of the patient (from a few inches to a foot or more), and this proximal portion is fixed in the same position and not articulable even when the cable is slacked. This allows the distal articulable portion of the arm to be shorter and allows the proximal portion of the arm (where the applied torque on the arm is magnified) to be more robust and rigid.

Various other types of adapters or components can alternatively be included to couple a desired tool to the arm. The distal tool adapter 25 as illustrated is mounted onto the distal head 40 of the last segment 22 of the arm. The tool adapter 25 includes a rounded recess at its base to receive the head 40 and allow for articulation therebetween. The retractor 24 is coupled to the adapter 25 with an end cap 43 and a nut 44 that attaches to the distal end of the cable 50. The cable 50 runs through the tool adapter 25 and retractor 24 and end cap 43, and applies compression back down the arm column through the nut 44 and optionally a washer or other additional components. The distal end of the cable 50 can also include an enlarged head that is larger than the opening in the distal-most part of the arm/adapter/tool to accomplish the application of compression along the arm. The distal tool can be quickly removed and added, such as to swap out a retractor with a different tool, by loosening the nut 44 and/or providing slack to the cable. In other embodiments, different types of adapters and related components can be used to provide a suitable coupling between a tool and the arm, such as various types of quick-release and quick-attach mechanisms, including but not limited to various types of specific purpose retractor blades, laparoscopic tool holders, and lighting devices.

Figure 16:
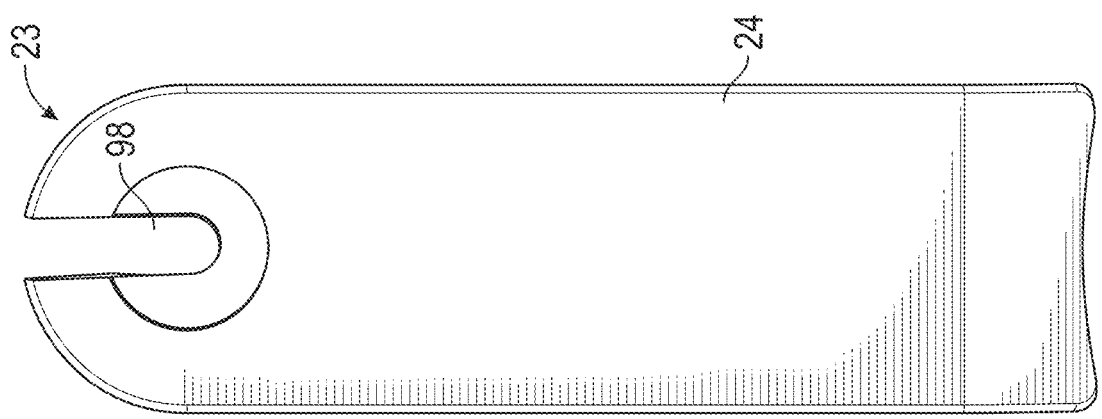
FIGS. 15 and 16 are views of an exemplary retainer attachment that is just one of many different kinds of tools that can be coupled to the distal end of the adjustable arm.
Figure 15:
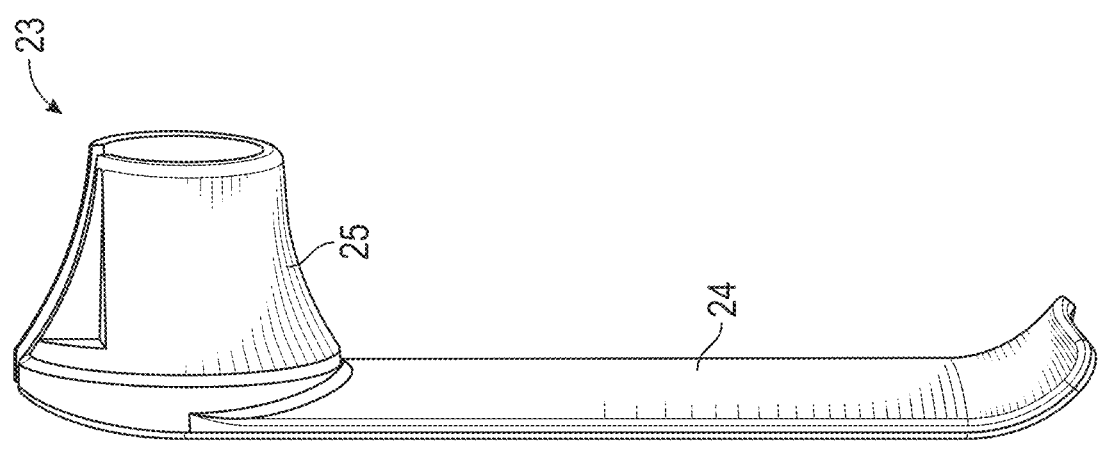

FIGS. 15 and 16 show an exemplary distal unit 23 that includes both the exemplary adapter 25 and retractor blade 24. The distal unit 23 is just one example of how a tool can be coupled to the distal end of the arm with an adapter, and many other tool coupling mechanisms can be included. Other adapters or coupling mechanisms can be included for retaining different types of blades, clamps, laparoscopic cameras, lighting devices, etc. Some adapters or coupling mechanism can include built-in/integrated lighting devices. The distal unit 23 includes a slot 98 extending through the adapter 25 that allows the cable 50 to be inserted laterally into the slot with its distal end extending out beyond the unit 23. A nut and/or washer larger than the width of the slot 98 can then be applied to the distal end of the cable to provide an end stop to prevent the cable from pulling through. Alternatively, a knob or other enlarged end portion of the cable can accomplish the same result. Then, when tension is applied to the cable, the nut/washer or enlarged end portion transfers tension in the cable to compression in the arm, making the arm rigid.

Figure 17:
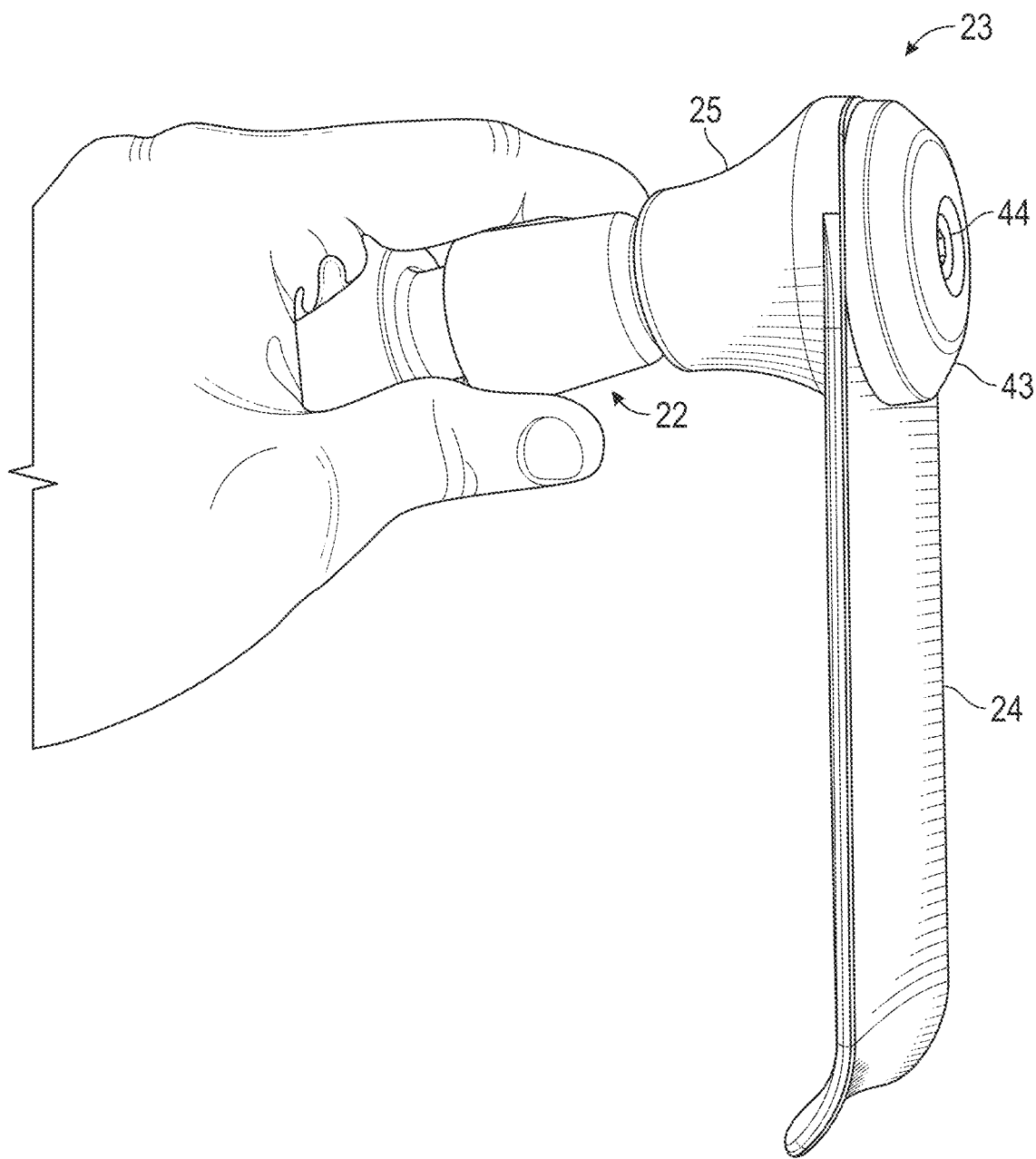
FIG. 17 shows the retainer attachment of FIG. 15 coupled to the distal end of the adjustable arm.
Figure 18:
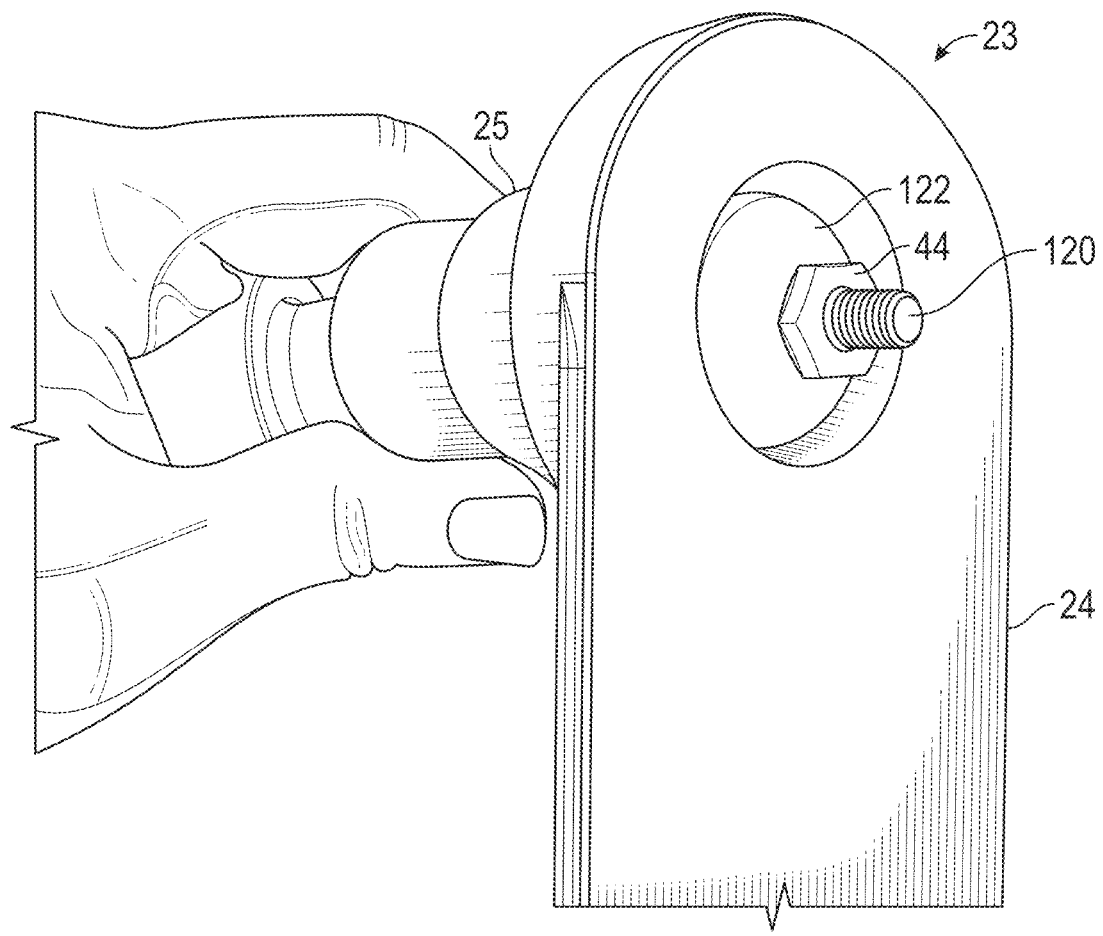
FIG. 18 shows the retainer attachment of FIG. 15 coupled to the distal end of the adjustable arm, with distal end cap removed for illustrative purposes.

FIG. 17 shows the distal end of the arm with the distal unit 23 secured between the last arm segment 22 and the nut 44 secured to the cable 50. The end cap 43 covers the end of the arm and can provide a smooth, rounded surface.

Figure 19:
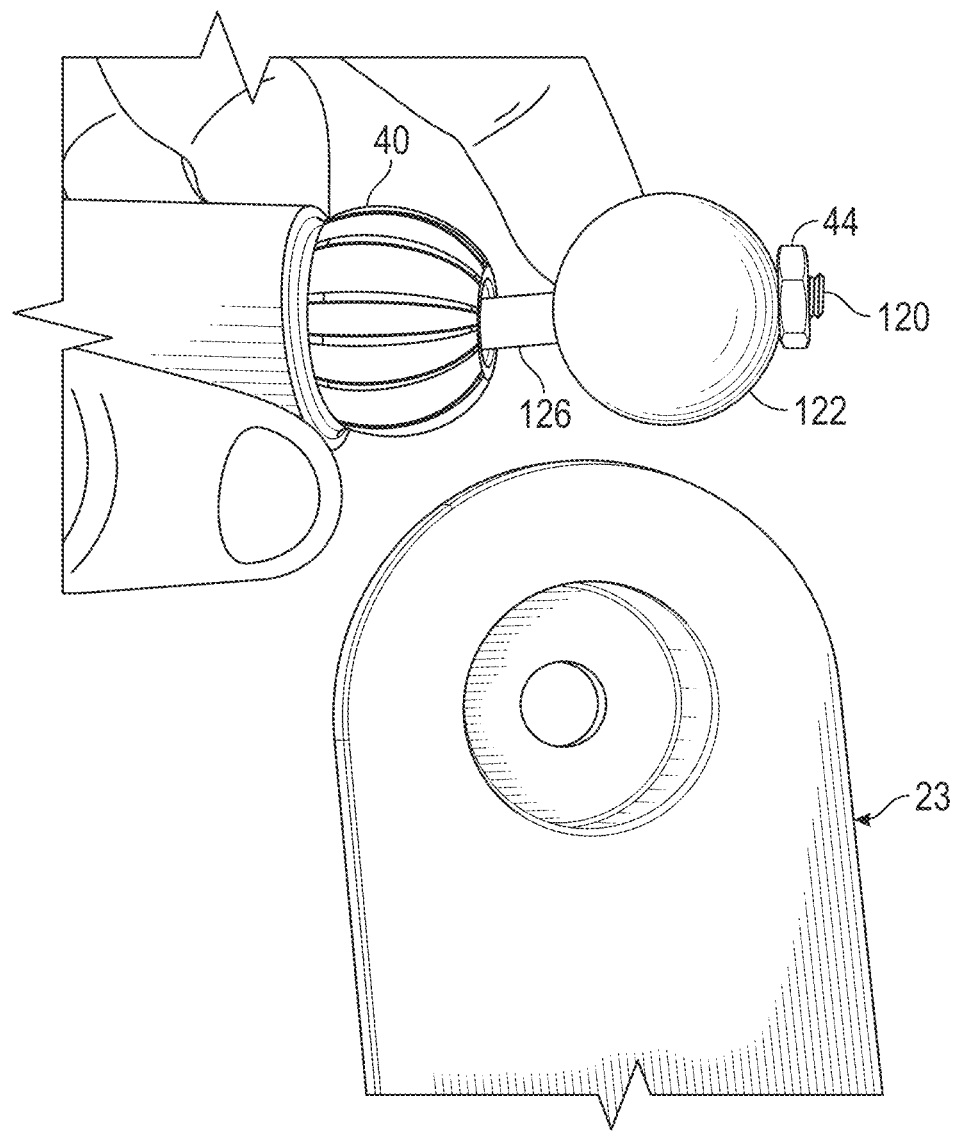
FIG. 19 shows the distal end of the adjustable arm with the retainer attachment removed, showing a portion of a tension cable running through the arm and a ball retainer and nut on the distal end of the cable.
Figure 20:
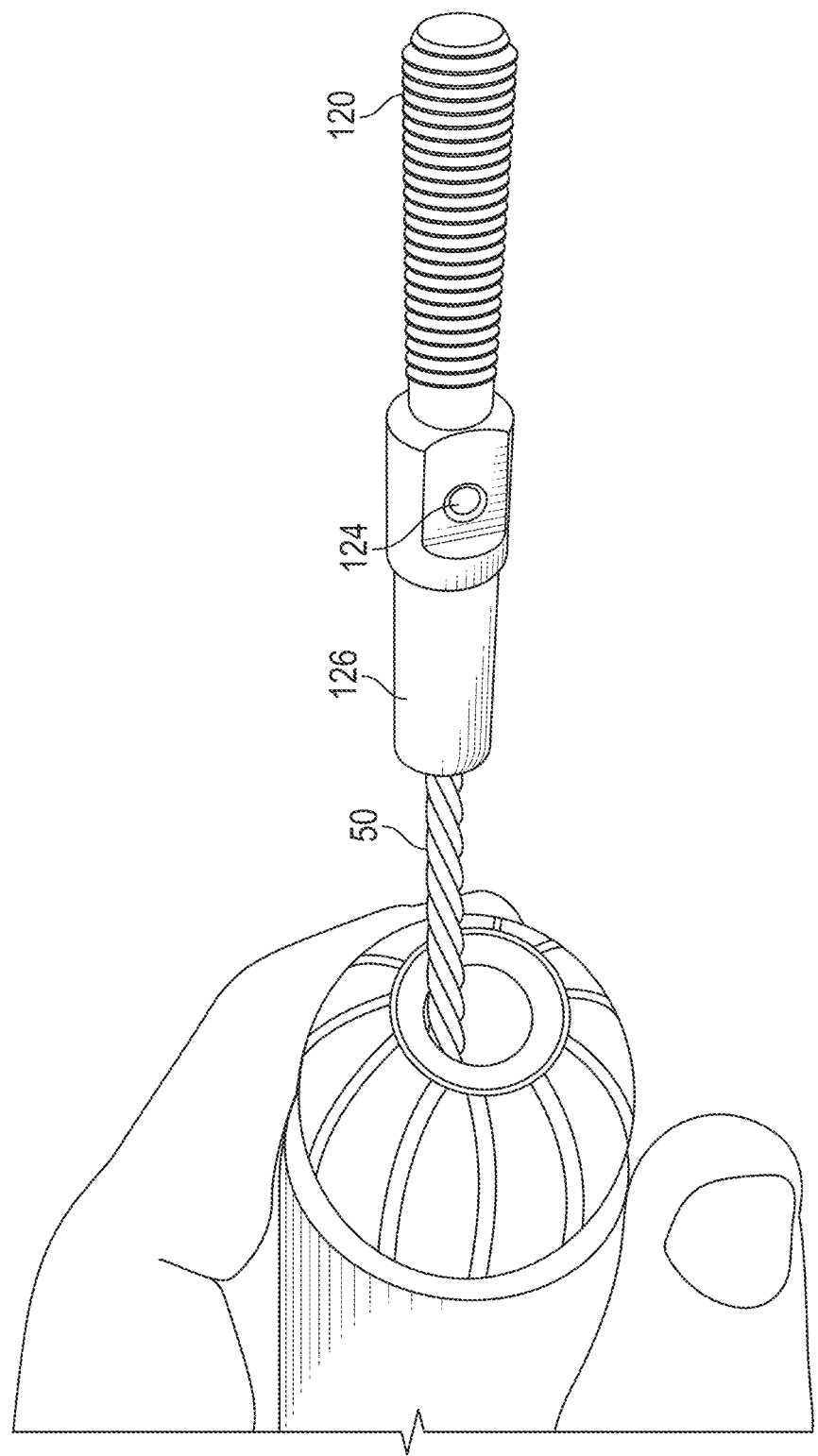
FIG. 20 shows the distal end of the tension cable extending from the adjustable arm.
Figure 21:
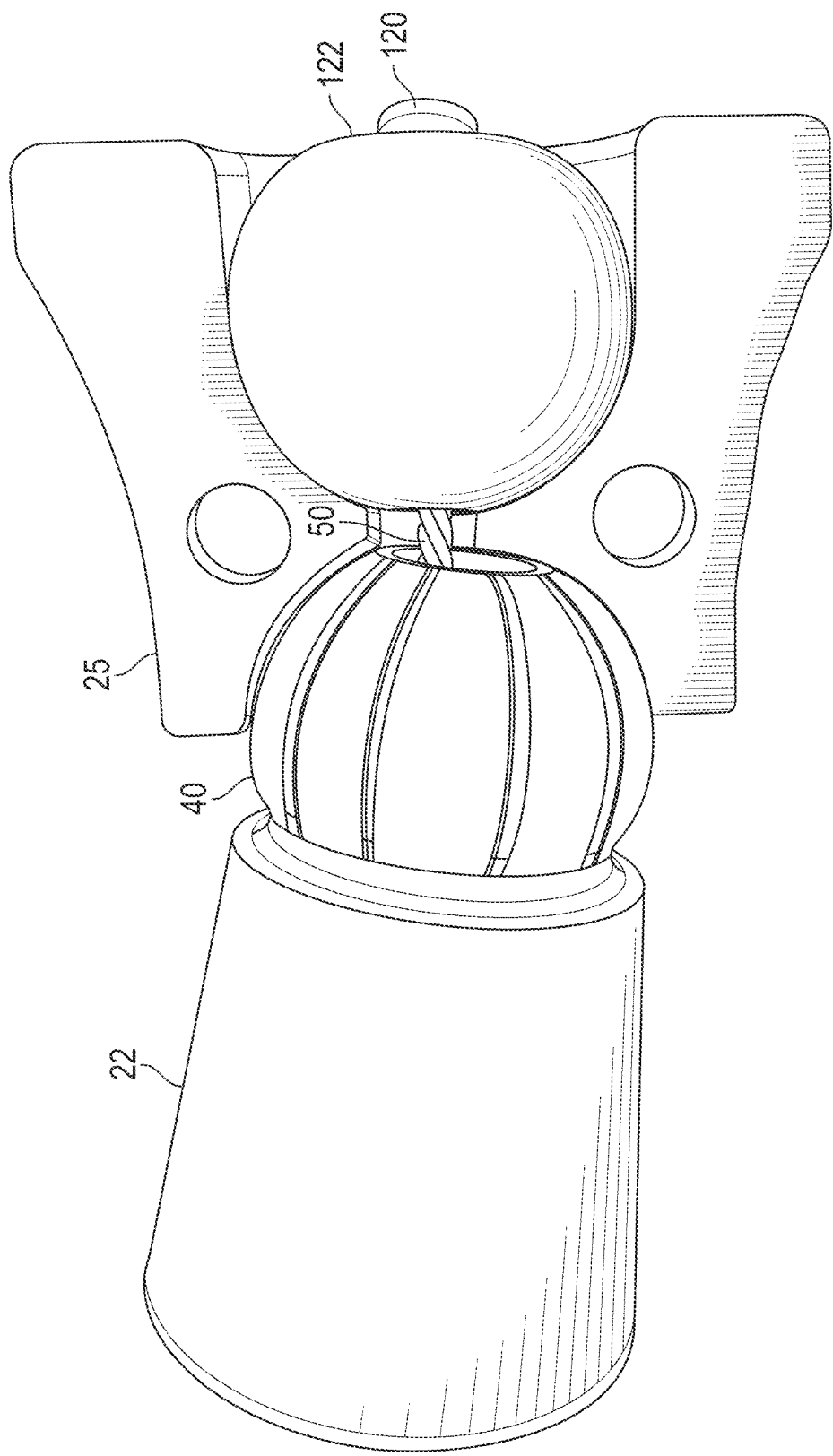
FIG. 21 shows a distal end portion of the adjustable arm with a distal attachment adapter split in half, with one half of the distal attachment adapter removed to illustrate its internal geometry.

FIGS. 18-21 illustrate an embodiment of the arm 20 and distal unit 23 that include a rounded (e.g., substantially spherical or ovoid) element, or ball, 122 around the end of the cable 50 that is positioned in a socket or recess in the adapter 25. The ball 122 allows the adapter 25 and blade 24 to pivot relative to the last segment 22 and transfer compression between the nut 22 and the adapter. As shown in FIG. 20, the distal end of the cable 50 can include a threaded portion 120 to receive the nut 44, and a cylindrical portion 126 that passes through the adapter 25 and ball 122. The portions from element 126 to the distal end of the cable 50 can be rigid relative to the more flexible majority of the cable. FIG. 19 shows the ball 122 and nut 44 mounted on the distal end of the cable 50 with the distal unit not attached. FIG. 21 shows how the distal head 40 of the last segment 22 and the ball 122 mount within the adapter 25 when assembled. In FIG. 21, half of the adapter 25 and the blade 24 are not shown for illustrative purposes. The head 40 engages within a proximal recess of the adapter and the ball 122 is positioned within a distal recess or socket of the adapter, with the cable 50 running through a narrow passage connecting the proximal and distal recesses in the adapter. The adapter 25 can be one piece or can comprise two halves that are fastened together around the ball 122. In this embodiment, compression from the cable 50 is transferred from the end of the distal end cable 120, to the nut 44, to the ball 122 (optionally through the blade 24 and/or end cap 43) in, to the adapter 25, to the head 40 of the last segment 22, through the rest of the segments 22 to the proximal end of the arm.

In some embodiments, adaptor 25 may be augmented or replaced with a quick-connect adapter that allows a user to attach and detach various different types of tools with a simple one step actuation, such as pressing a button or lever, pulling a sheath back, twisting a collar, etc. For example, the adaptor my permit the attachment of standard, metal retractor blades. The same or a different adaptor may permit attachment of a laparoscopic camera or lighting device.

The arm 20 can be an independent part of the overall system, and can be detachable from and re-attachable to the stationary box 30 and the rest of the system, such as for purposes of sterilization and quick set-up. In some embodiments, the arm 20 may be a disposable component delivered to the operating room ("OR") in a sterile package. All components of the arm 20 can be made of materials which can be surgically sterilized and/or manufactured in a sterile manner.

Figure 5:
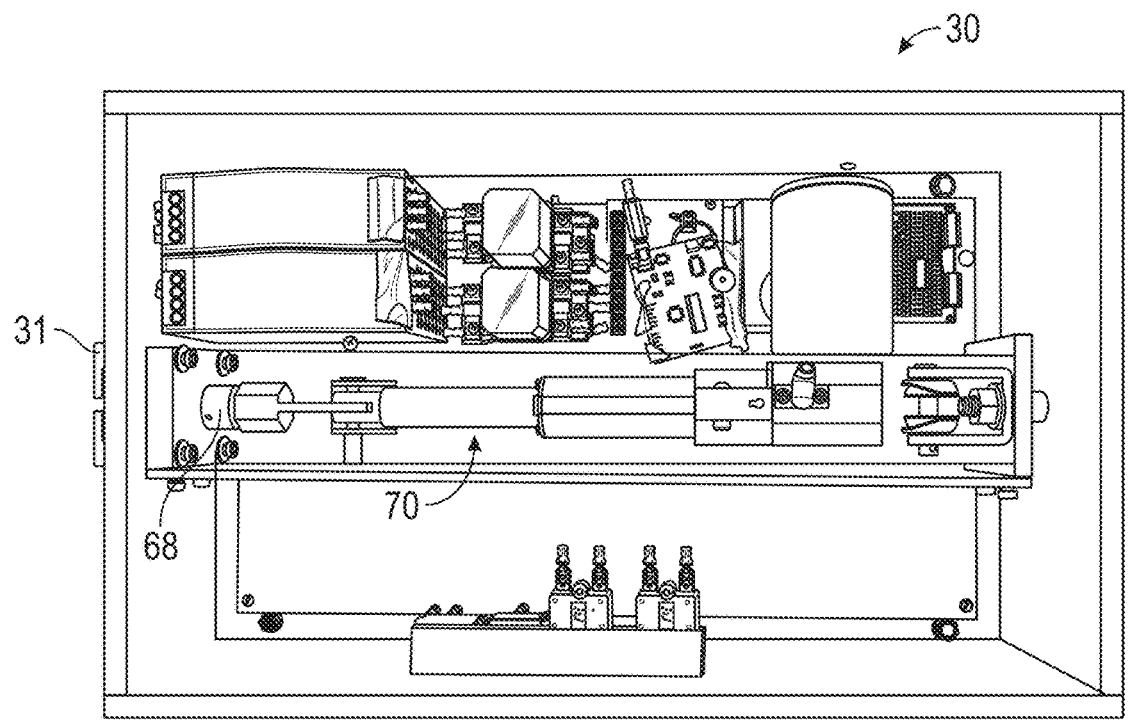
FIG. 5 is a view of internals of an exemplary actuation and control unit (wires not shown for clarity).

When used, the proximal adapter 26 of the arm 20 can attach to a stationary mounting platform 28, which can be part of or coupled to the box 30 that houses actuation and control components. The box 30 can include a motor and/or other actuation device 70 (FIG. 5) that selectively applies a desired tension on the tension cable 50 running through the arm 20. The box can also house electronics, computing and control components, power source components, sensors, and/or other components.

Figure 4:
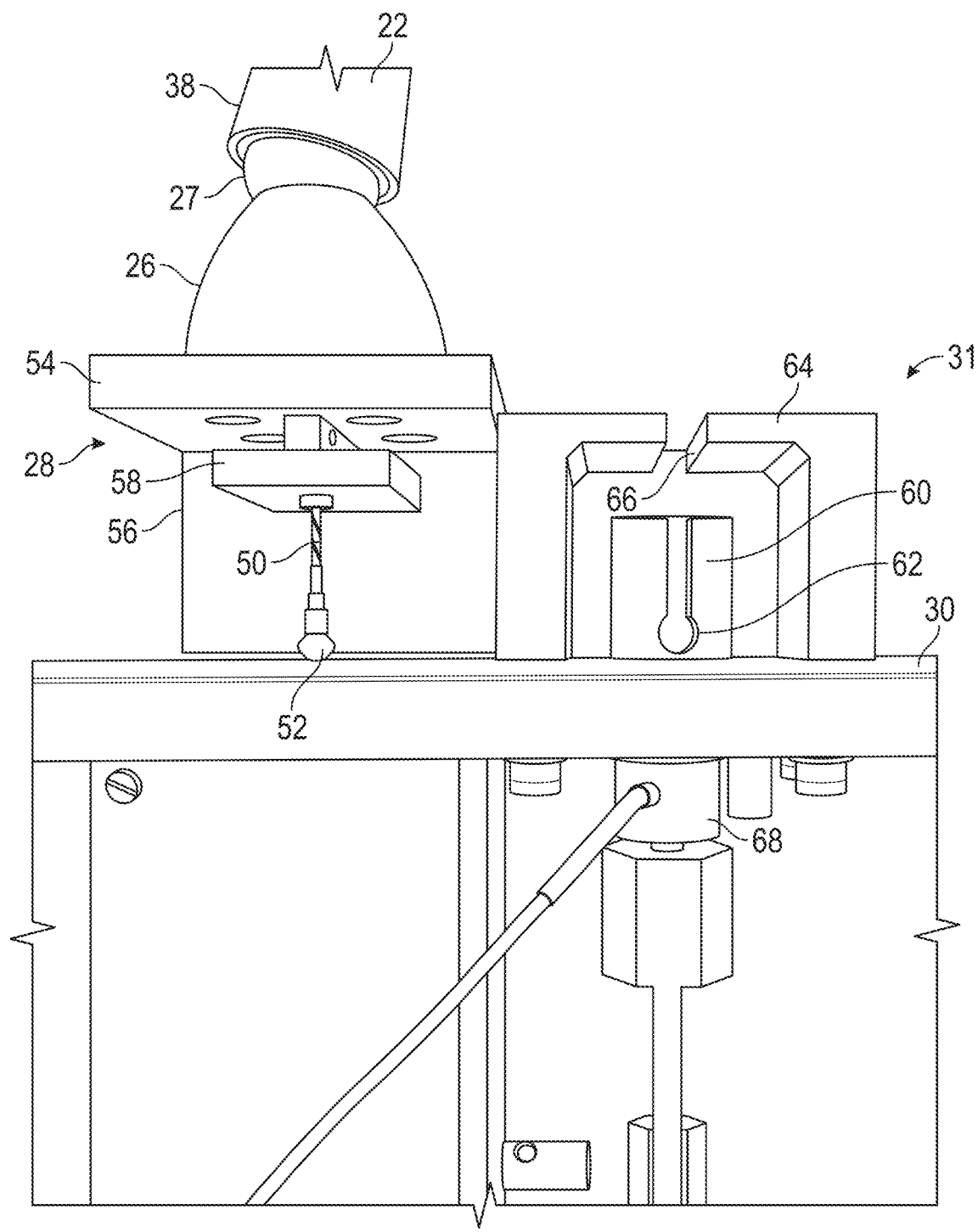
FIG. 4 is a detailed view of an interface between the proximal end of the arm and the top of the actuation and control unit.

In some embodiments, the box 30 can comprise mounting features that are configured to connect to the proximal end of the arm 20 such that the actuation components inside the box are functionally coupled to the tension cable 50 and the base of the arm is held stationary. As shown in FIG. 4, the box 30 includes an arm mount 31 at the top of the box that is configured to be attached to the mounting platform 28 at the proximal end of the arm 20. The mounting platform 28 is fixedly coupled to the proximal adapter 26 of the arm, which is articulably coupled to the most proximal one of the several segments 22 that form the majority of the length of the arm.

Figure 12:
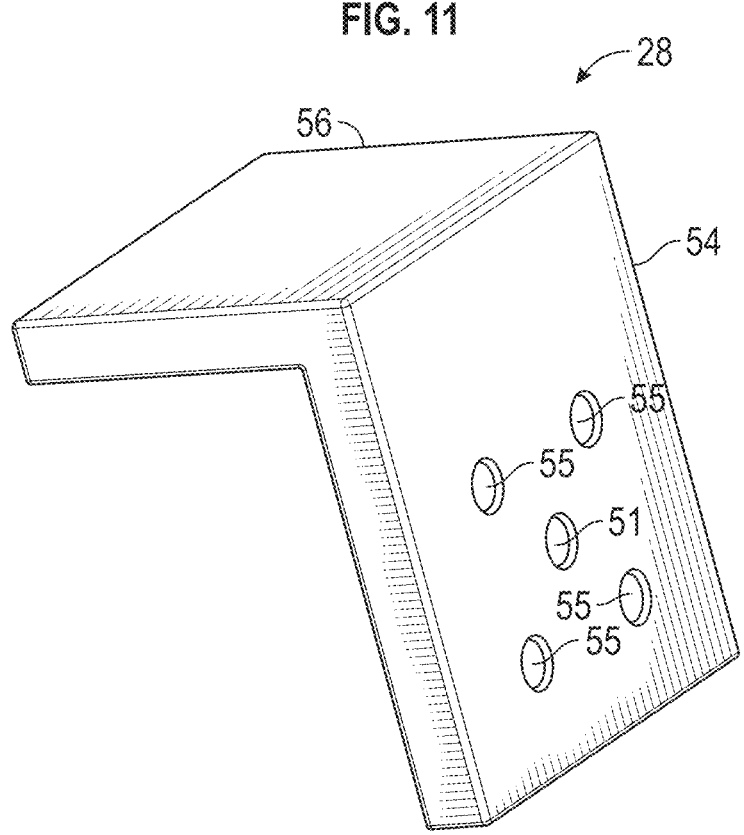
Figure 13:
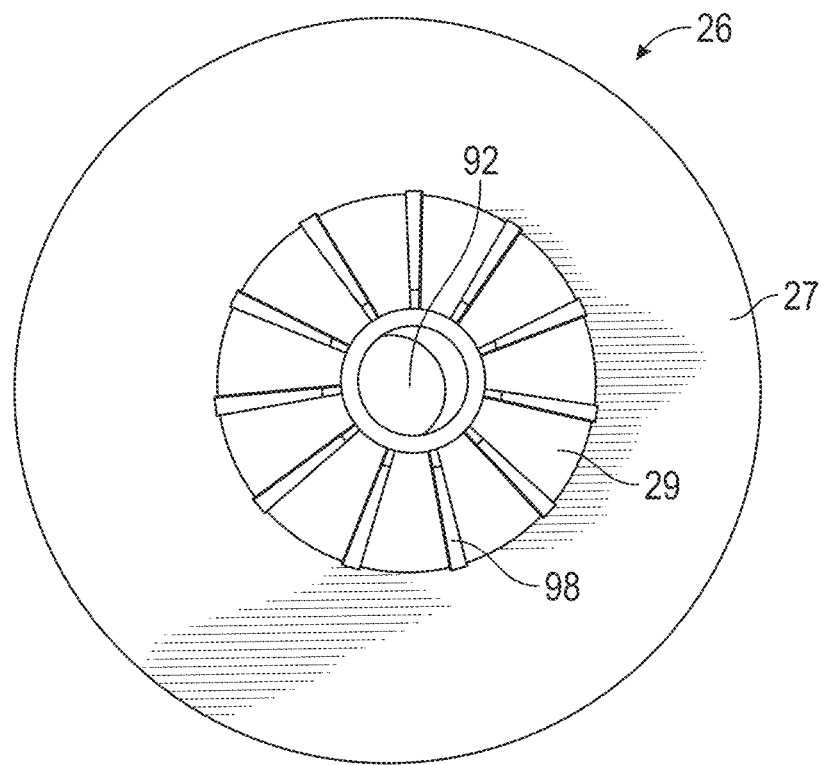
FIG. 13 is a top view of a proximal adapter that couples the adjustable portion of the arm to the arm attachment component of FIGS. 11 and 12.
Figure 14:
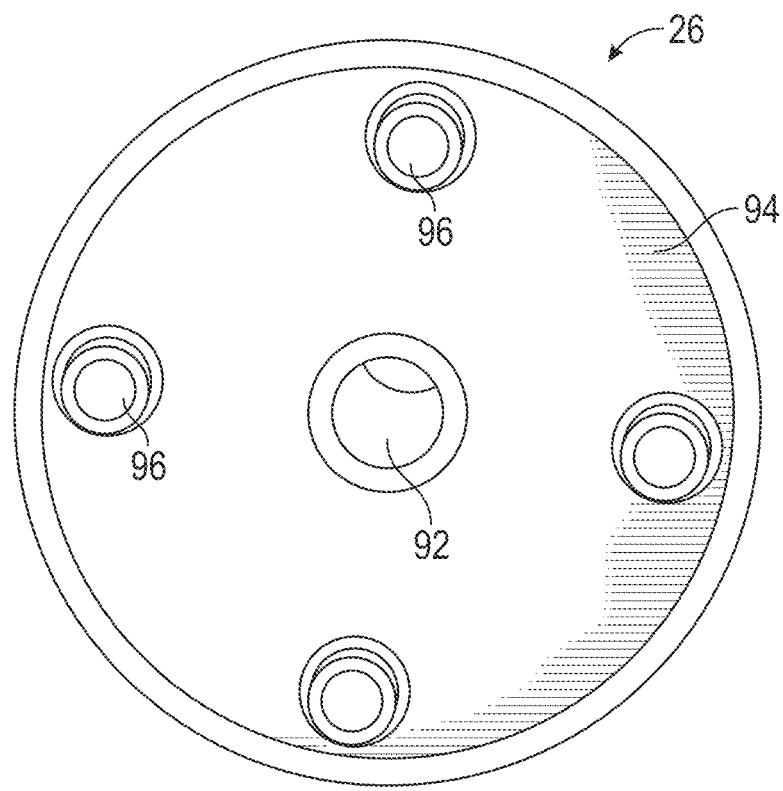
FIG. 14 is a bottom view of the proximal adapter of FIG. 13.

The proximal adapter 26 is shown in more detail in FIGS. 13 and 14, and comprises a base portion 27 having a rounded (e.g., spherical) upper surface, and an upper portion 29 having a rounded (e.g., spherical) outer surface that is positioned in a corresponding receiving opening in one of the segments 22. The outer surface of the upper portion 29 can optionally include surface roughness, ridges, grooves, or other motion-preventing features 98 (FIG. 13). The bottom of the base portion 27 can include two or more feet 96 (FIG. 14) that can be fixedly inserted into corresponding holes 55 in the mounting platform 28 (FIG. 12), such as by using screws, snap fit, or retaining means, such that the proximal adapter 26 is fixed in position relative to the mounting platform 28 and a central passageway 92 of the proximal adapter is aligned with a central opening 51 in the mounting platform to allow passage of the cable 50. The proximal adapter and the mounting platform can also include electrical, optical, or other connections, such as to couple wires or optical fibers running along the arm to components on or in the box 30. For example, the proximal adapter and/or the mounting platform can include contacts that mate with each other to electrically couple electrical conduits when the arm is assembled and mounted to the box 30. Similarly, the arm mount 31 on the top of the box 30 can also include electrical, optical, or other connections that couple with corresponding features of the mounting platform. Such connections can enable various tools to be used with the arm, such as lights, cameras, and other powered tools.

Figure 11:
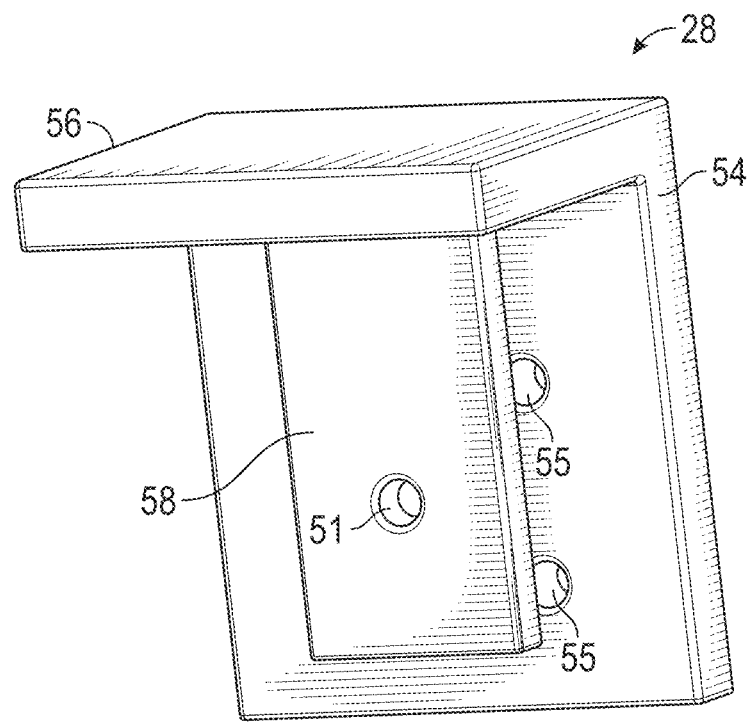
FIGS. 11 and 12 are perspective views of arm attachment component that couples an adjustable arm to receiving component of an actuation and control unit.

The exemplary mounting platform 28 is shown in more detail in FIGS. 11 and 12, and comprises a top plate 54, rear plate 56, and engagement member 58. As shown in FIG. 4, the exemplary arm mount 31 on the top of the box 30 can include a stationary, open-sided rectangular outer wall 64 with a slot 66 in the top of the outer wall, and a movable, cable engagement element 60 with a cable receiving slot 62 in the side of the element 60. In this exemplary embodiment, when the mounting platform 28 is attached to the arm mount 31, a ball, knob, or other enlarged proximal end features 52 of the cable is inserted laterally into the slot 62, the engagement member 58 of the mounting platform 28 is inserted laterally under the outer wall 64, and the upper plate 54 of the mounting platform goes over the top of the outer wall 64. In this engaged position, the mounting platform 28 is fixed in position relative to the arm mount 31 and the rest of the box 30. Screws, other fasteners, a friction fit, a snap fit, cable pretension, and/or other means can further be used to hold the mounting platform in engagement with the arm mount 31. In other embodiments, the arm and cable can be coupled and decoupled from the box and actuator in various different arrangements.

The engagement mechanism between the mounting platform 28 and the arm mount 31 can be configured to be engaged through a surgical drape or other sheet of material, such that the box 30 and arm mount 31 can be located under/beneath the drape and the arm 20 including the mounting platform 28 can be located above the drape. In this way, the box and arm mount do not need to be sterile. In some embodiments, the engagement of the arm to the box includes cutting or ripping through the surgical drape before or when the mounting platform 28 and the arm mount 31 are engaged together. In other embodiments, the drape can be captured or pinched between the upper plate 54 of the mounting platform 28 and the upper wall 64 of the arm mount 31, without restricting the engagement between the arm 20 and the box 30.

The cable 50 extends down through passageways 47 and 48 in the segments 22 (FIG. 9), through passageway 92 in the proximal adapter 26 (FIG. 13), through opening 51 in the mounting platform (FIG. 11), and extends to the enlarged proximal end feature 52 that is engaged within the slot 62 (FIG. 4). The slot 62 can have a narrowed upper part that is wide enough for the cable 50 to pass through, but narrower than the enlarged proximal end feature 52. From the positions shown in in FIG. 4, the platform 28 or the arm mount 31 would first need to be turned around 180° to engage with each other.

The cable engagement element 60 inside the arm mount 31 can be part of or coupled to an actuator 70 inside the box 30 (FIG. 5) such that the actuator 70 can pull down on the cable 50 via the cable engagement element 60 while holding the rest of the arm 20 stationary to apply a desired amount of tension to the cable and thereby a desired amount of compression along the length of the arm 20. A force or tension sensor 68 can also be included between the actuator 70 and the cable engagement element 60 and coupled to a processor or control unit to measure the amount of tension applied to the cable 50.

In some embodiments, the tensioning system can include a safety feature that allows automatic tension release on the cable under certain circumstances, such as if too much tension is sensed on the cable. For example, the actuator 70 or cable engagement element 60 can include a shear pin that is designed to fail if too much force is applied to it, such that the actuator is decoupled from the cable when the shear pin fails, releasing tension on the cable. This can prevent damage to the arm system and/or damage to the patient.

The box 30 can also include a clamp 32 or other adapter that couples the box to a side rail 16 or other rigid component of a surgical table 14 (FIG. 1). The box 30 can also comprise or be coupled to an electrical power cable which plugs into a standard power outlet or other power source. In some embodiments, the box 30 can include a port or electrical cable that is coupled to a foot pedal 34 (or other user input spaced from the box 30) so a user can control the device, at least in part, using input from a foot or hand. The box 30 can contain an actuator 70 to apply tension on the cable 50, a force or tension measuring sensor 68, power supply, a microprocessor, digital logic device, or other computing hardware, control and signal conditioning electronics for the apparatus, and/or other components. The actuator 70 can utilize any suitable design, such as electric, mechanical, pneumatic, magnetic, and/or other types of actuation mechanisms. Exemplary actuator components can include a worm gear, a linear actuator, a pneumatic actuator, an electromagnetic actuator, a hydraulic actuator, and a winch and spool actuator.

In particular embodiments, the actuator 70 can comprise a pneumatic actuator and the system can include related pneumatic components. For example, the box can contain a pressure regulator, solenoid valves, spool valves, pneumatic hosing, pneumatic cylinders/pistons, couples, etc. In such embodiments, a force/tension sensor (like the sensor 68) is needed but can be included as well. With a pneumatic system, applied force can be determined by a pressure regulator, such a manual, electronic, or digitally programmable pressure regulator. An additional tension sensor between the actuator and the cable can be used as for safety override purposes, or closed loop control. In a pneumatic system, the force can be controlled by regulating the pressure such that the pressure times the area of the pneumatic piston provides a suitable force. Pneumatic actuators can utilize any type of working gas, such as air, nitrogen, etc.

As described above, the box 30 can be configured to attach tightly to the side rail 16 or other component of an operating table 14 through use of clamp or hook 32 or other fastening mechanism, which can fix the box's location in terms of both translation and rotation relative to the table. In some embodiments, the clamp or hook 32 can allow the box 30 to slide along the side rail to different locations along the surgical table, then be fixed in place at a desired location. In some embodiments, the box 30 can include two or more arm mounts each with their own actuators, such that a single rigid support can provide for two independent adjustable arm systems. More than one of the boxes 30 can also be attached the same table at the same time, either to allow for multiple of the disclosed arms to be used at the same time, or allow multiple options for where a user can attach a single arm, which can save time in setting up the arm by not having to relocate the box.

The box 30 and its components do not need to be sterilized as they can be placed on the surgical rail 16 below and/or to the side of the sterile field. The box 30 can provide a stable mounting point for the arm 20. The mounting interface components 28 and 31 can connect the arm 20 to the rigid box, holding the arm securely in place and allowing for the actuation components of the box to pull on the cable 50 running through the arm. In some embodiments, the box can connect the cable 50 to the actuator 70 in series with a force/tension sensor 68. This allows for measurement of tension on the cable running through the arm. Thus, when the arm is attached to the box, the cable can be pulled by downward motion of the actuator, and the tensile force can be measured by the sensor 68. The actuator 70 and the control system can be configured to automatically apply a desired amount of tension to the cable (e.g., a predetermined tension force or a user selected tension force) using the feedback from the sensor 68. Similarly, the control system and force sensor could work in conjunction with an electronically controlled pneumatic pressure regulator in the case of a pneumatic actuator to provide a predetermined force. In some embodiments, the actuator 70 can apply more than one different tension levels depending on certain conditions. For example, a zero tension or loose setting for setting up the arm, one or more full tension settings for holding the arm rigid during surgery (e.g., there can be more than one full tension setting for different operating conditions or the number of tools attached to the arm or the length of the arm, etc.), an intermediate tension setting that is sufficient to hold the arm in a suspended state overcoming gravity without a load on the retractor but weak enough to allow the user to manually adjust the position of the arm, and/or other tensioning modes.

The arm mounting components 28 and 31 can also be designed in such a way as to allow for rapid attachment and detachment of the sterile surgical arm 20 to the box 30. The box 30 can also contain electronic components to power the actuator, interpret signals from any force sensor and/or user inputs, and control the system based on the input information.

Figure 22:
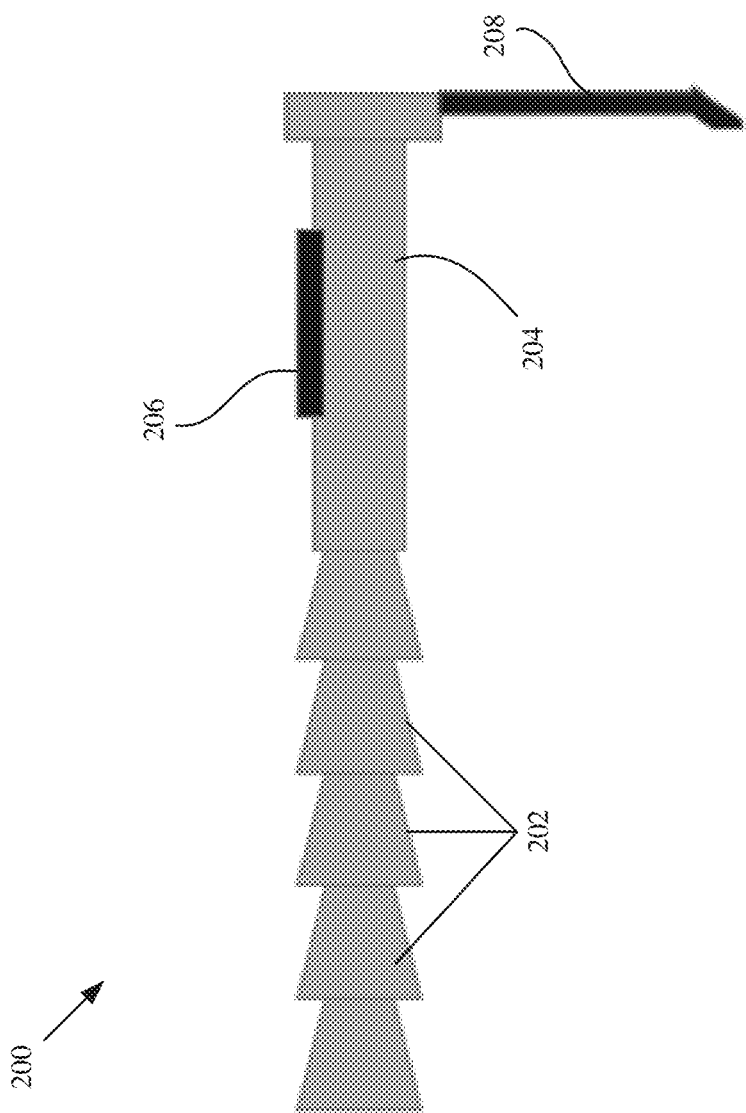
FIG. 22 shows a distal portion of an exemplary arm including a handle with a release switch.

In some embodiments, the user input mechanism can comprise a hand-actuated input device (button, switch, lever, touch surface, etc.) on the arm 20. FIG. 22 illustrates an exemplary arm 200 that includes a switch 206 positioned on a handle 204 at or near a distal end of the arm segments 202. For example, such a switch 206 can be actuated to release or tension the arm, in some embodiments. The same handle 204 can function as an adapter to hold a tool 208. In this way, a user's hands can remain as close as possible to the surgical site. A user can grasp the handle 204 near the distal end of the arm 200, loosen the arm with one touch of the switch 206, move the distal portion of the arm and the attached tool 208 to a desired location relative to the surgical site, and then make the arm rigid again with another touch or the release of the switch. The handle 204 can also include a tool release mechanism that allows a user to quickly detach the tool 208 from the handle 204 and quickly attach a tool to the handle. In some embodiments, a switch such as the switch 206 can be used to release a tool from the handle, to control a light source on the arm, to control a camera device on the arm, and/or to perform various other functions related to tools coupled to the arm. More than one switch such as switch 206 can be present on the arm to perform various different functions, such as one switch to release and tension the arm, another switch to release a tool from the arm, and/or another switch to turn a light on the arm on and off. The switch 206 can also comprise a variable actuation, such as allowing a user to control the amount of tension in the arm over a variable range. For example, depressing a button longer or pressing harder can result in increased tension in the arm.

The input signal from pressing on the foot pedal 34 or other user input (e.g., a button on the base of the arm) can be used by the control system logic in determining when to take some action. In some embodiments, for example, pressing the foot pedal 34 sends a signal to the control system, causing the actuator 70 to tighten or loosen the cable 50 as appropriate. When the tension cable 50 is tightened by the actuator 70, such as by tapping on the pedal 34 once, the cable pulls the components of the arm 20 together. Friction between the components 22, 25, 26, etc., of the arm 20 increases with tension on the cable 50, and mechanical interlocking can also occur, causing the arm to become rigid. The nominal positions of the arm's segments can be fixed relative to one another when the cable 50 is under sufficient tension, even when external loads are applied to the arm. Tapping the foot pedal 34 again (or releasing the foot pedal) can release the tension in the cable and loosen the arm, causing it to become flexible again. This allows for rapid adjustment of the arm during surgery. In some embodiments, a residual tension can remain in the cable during the "loose" state such that the arm is semi-rigid and stays in place versus just gravity, but can be readily repositioned by manual force by the user.

During a conventional emergency open surgery operation (e.g., surgery which utilizes a large incision for direct visualization and manipulation of tissue), the abdomen is opened and single- or two-point retraction is typically attained with hand-held retractors. Afterwards, time is taken to set up the Bookwalter retractor or other similar devices to allow for hands-free operating. The device is adjusted throughout the surgery as necessary, again requiring the hands of both the surgeon and an assistant. This scenario changes when the disclosed system is used. In one example, the box 30 is already attached to the OR table before the procedure begins or even before the patient is moved onto the table if desired. Alternatively, the box stays attached to the OR table, even in between cases so that it is available at a moment's notice during any operation. Once the surgical field is established, the sterile arm can be attached to the box when needed or before the opening incision is made. The arm can be laid to the side until it is needed. In one example, the abdomen or other anatomical feature is opened and the surgeon uses the arm for single-point retraction (e.g., FIG. 6), but then he or she can seamlessly transition to multiple point retraction (e.g., FIG. 7) with minimal effort. In one example, when more retraction is desired, the surgeon can simply add another retractor blade to the arm and position the arm accordingly with one or two touches of the foot pedal 34, pressing a button on the arm, or similar activation of other user input devices. Further, if the surgeon desires multi-point retraction (e.g., four or five point retraction), the arm can be shaped into a circular or semicircular ring around the surgical area, and again the user input can be pressed with the foot or hand, locking a curled arm into place and allowing for the addition of multiple retractors or other tools in any position.

The disclosed technology provides many advantages. For example, manual retraction cannot feasibly provide prolonged five-point retraction and a Bookwalter is too obtrusive to be used for single-point retraction, necessitating a mid-surgery transition. The disclosed system obviates the transition and improves both single-point and multi-point retraction. The disclosed system can provide the same benefit as manual single point retraction, but can also satisfy the aforementioned deficiencies: hands-free retraction and maintenance of tension over time. With the disclosed system, single or multi-point retraction can be applied from any angle or location, including deep within the abdominal or pelvic cavities. Adjusting the retractor can be done very easily, only requiring pressing of the foot pedal to loosen the arm, repositioning the retractor as desired, and pressing the foot pedal again (or holding and releasing the pedal) to make the arm rigid again. Because the arm can be long and is flexible in the relaxed state, it can be attached to the OR table at any point, retract in any direction, and be placed in such a manner that it is unobtrusive to the surgeon and assistants. Furthermore, a retractor or other tool can be much faster to deploy using the disclosed system than with conventional solutions, without having to spend time with meticulous positioning of a ring or frame. The system can also optionally provide lighting with, for example, the addition of a fiber-optic lighting system or integrated LED lighting.

In some embodiments, the disclosed system can include a lighting and/or imaging system. For example, a fiberoptic cable can run through or along the arm to position a light source or camera lens at the distal end of the arm. In some embodiments, an electric LED light or lights can be positioned near the distal end of the arm and have a self-contained battery pack or one or more wires that run proximally from the LED light, such as down the arm, to a power source, such as the power supply inside the box 30, or other device. The imaging/light cord cable can attach to a light source or imaging processor inside or in the proximity of the box 30, for example. The inclusion of a localized lighting system can be of great value to the surgeon as achieving adequate tissue lighting is a continual challenge, particularly deep within the abdominal and pelvic cavities. This also removes an additional device or devices near the operating area that can clutter the space and impede the operation, and can also reduce fatigue of surgeons wearing head-mounted lighting.

Various alternative embodiments and configurations of the disclosed system can offer additional flexibility in the progression of surgery. For example, a surgeon might elect to use multiple of the disclosed arms each configured as single-point retractors, or some combination of single-point and multi-point retractors, or even combine the articulable arm retractor system with existing retractor systems such as the Bookwalter in order to achieve retraction of tissues, such as deep within the abdominal cavity.

For use in minimally invasive surgery, embodiments of the disclosed system can have an attachment capable of holding a laparoscopic/thoracoscopic camera or any of the minimally invasive surgical instruments used with such procedures. In laparoscopic or thoracoscopic surgery, the same retractor arm or other tool attachment can provide a stable camera support that is easily adjustable. The retractor arm can free up the hand of an assistant or surgeon. This can also allow for some operations such as the laparoscopic appendectomy (previously requiring a surgeon, an assistant, and a tech) to be performed without an assistant (e.g., just the surgeon, the tech, and the retractor arm). Because the box can be perpetually attached to the OR table, the arm can be available for any case which requires it, including the midnight appendectomy or other similar understaffed case. This would free up additional personnel to manage other medical duties, reducing cost and improving care for others.

Additional advantages and benefits of the disclosed technology (e.g., when used to hold retractors) over conventional technology can include improved visualization of the target area, enhanced ability to provide retraction in almost any space and at almost any angle, easier adjustability of the retractor, quicker set-up time, hands-free maintenance of tissue retraction, and no loss of tension on the tissue over prolonged periods of time. In manual retraction, each retractor occupies a hand, and prolonged retraction results in fatigue creating suboptimal retraction and shaky-handed manual holders. Currently available surgical retractors fail to provide one or more of these advantages.

The length and strength of the disclosed arms can be significantly greater than other conventional devices, and the disclosed arms are configured to remain rigid while supporting substantially more weight/forces than conventional devices. This is made possible in part by the unique design of the individual segments that make up the arm. The size and shape of each segment is configured to increase the compressive and frictional forces that hold the rigidity of the arm at each joint without significantly hindering arm flexibility when loosened. Additionally, the inclusion of joint surface texturing, ridges, or similar features, in certain embodiments increases the friction and interlocking between each pair of segments, further improving arm strength under load.

With the disclosed systems, there can be little or no practical restriction as to the retractors' locations or angles, such as there is with the Bookwalter device where retraction can only occur radially outward with respect to the ring contour. With the disclosed device, retraction can occur from just about any angle or location, including deep within the abdominal or pelvic cavities. Deploying and adjusting the retractor can be done very easily, e.g., only requiring pressing or releasing the foot pedal or other switch to loosen the arm, repositioning the attached tool as desired, and releasing or pressing the foot pedal or switch a second time to make it rigid again.

The device is capable of being used for laparoscopic, thoracoscopic, orthoscopic, open surgery, and/or other procedures without having to change out for a different device. This can be especially convenient during cases where laparoscopy is used to start the case, but later abandoned for an open surgical approach. In these cases, the retractor arm can functionally transition from "camera support arm" to "open surgical retractor" just by changing the attachment on the end of the retractor arm.

The disclosed devices can not only to hold a single retractor at the end of the column as in conventional retaining devices, but can also allow seamless transition to multi-point retraction by adding retractors to the shaft of the column. This feature can be enabled by the inclusion of specifically designed linkages or segments that make up the arm. Conventional articulable columns used in surgery typically only place a tool at the distal end of the arm. By contrast, the disclosed adjustable arm can be significantly longer than conventional articulable columns and can provides a means for creating a custom fitting ring or semi-ring around an open abdominal incision with retraction occurring in any number of directions by adding retractors to the shaft of the articulable column. Unlike conventional devices, the disclosed devices can provide an articulable column capable of forming a ring or semi-ring shaped retainer appropriate for any size or shaped incision, and can allow for the addition of multiple retractor heads to various points along the shaft of the articulable column.

Furthermore, unlike conventional devices, the disclosed devices can allow for rapid and simple disconnection of the arm from the stationary actuator box, which allows for more rapid deployment by having the motor box already mounted on the operating table at the beginning of the operation. In addition, the disclosed devices can include one or more force sensors to monitor the tension on the cable.

Additional novel aspects of the device relate to the length and strength of the articulable column used as the retractor arm. An adjustable retainer arm suitable for a hands-free abdominal retraction system has much greater requirements compared to other procedures where retainer arms have been used, such as in cranial surgery. With some embodiments disclosed herein, the arm can be able to support not only its own weight, but the greater forces required for retraction of tissue and internal organs such as the liver. Typical retraction forces can approach 10-20 pounds, which can be far higher than the forces seen by conventional articulable column devices. The longer arm length and the higher applied forces can also require a higher internal cable tension to keep the arm rigid. The maximum sustainable static friction force between two surfaces is typically proportional to the applied normal force between the surfaces. For this reason, and to be effective in a trauma situation, a high magnitude force may need to be applied to the column's central cable very quickly. In some embodiments, the cable can be loaded with at least 50 pounds, at least 100 pounds, at least 150 pounds, at least 200 pounds, at least 250 pounds, at least 300 pounds, at least 400 pounds, at least 600 pounds, and/or at least 800 pounds of tension. At the same time, the joint design of the disclosed devices greatly reduces the required cable tension needed for a given holding force. Thicker cables can be used to handle greater tension levels, while still being flexible enough to allow full flexibility of the arm when not loaded. The inherent cable stiffness, in conjunction with the pretension or residual tension on the cable can permit the configurability of the arm in the relaxed state to be tailored for a particular procedure or field of use.

The ability to handle such a high load capacity over a long arm length is a result of many features of the device, some of which include the column segment design, including material and manufacturing process selection and advantageous surface texture or mechanical interlocking within the joints. The disclosed devices can include light-weight, high-strength arm segments comprising materials suitable for the device's requirements. The segments can be sufficiently lightweight to minimize the effects of gravitational weight on the column's maximum load capacity. In different embodiments, any suitable strong materials can be used, including polymeric materials, metals, alloys, composite materials (e.g., carbon fiber reinforced polymeric materials), etc. Especially suitable materials can include polymeric or composite materials that are injection moldable or 3D printable, and biocompatible. Furthermore, the arm segments can include surfaces that mechanically interlock or interfere with each other in such a way that the segments can resist rotation both orthogonal to and about the longitudinal axis of the arm when under tension, and result in a substantial increase in the column's maximum load capacity.

In some embodiments, the arm and/or attachable tools can comprise or support other devices, such as fiber-optics or LED lighting systems, which can provide high-intensity and/or low-temperature lighting to the target tissues deep within the abdominal, pelvic, or thoracic cavities. In some embodiments, the arm and/or attachable tools can comprise or support optical imaging systems, such as to provide live video of the surgical location on a monitor in the operating room. Such optical and imaging components can include cords or wires that run along the outside of the segments 22 or through the middle of the segments next to the cable 50, or optionally through other channels formed within the links. When inside the segments, the design can be selected to avoid pinching or shearing the cords or wires when the arm articulates. When outside the segments, the cords or wires can be contained along with the arm segments inside a sheath, or the cords or wires can be coupled to the arm segments by ties or bands or other retainers. The proximal ends of the imaging/lighting cords or wires can terminate inside the box 30 or at any other location where a light source and/or imaging receiver may be located.

In some embodiments, the systems disclosed herein can be configured to provide audible or visual outputs, such as beeps or other sounds, lights, etc., to indicate the status of the system or other conditions. For example, an audible or visible indication can be made when the foot pedal or other user input is actuated, when full tension is achieved in the cable, etc.

The technology disclosed herein can also be used outside of the realm of surgery, such as in various other non-surgical medical procedures where a tool or device needs to be held in a rigid stationary position. Still further, the disclosed technology can be used outside of the medical field, such as in other industries where subjects (e.g., human or non-human objects) are held in a stationary positions. For example, the disclosed technology can be used in industrial and manufacturing processes where devices or objects are assembled, worked upon, or held. Accordingly, this disclosure is not limited to those particular embodiments disclosed herein that are configured for surgical applications or even medical applications.

Figure 32:
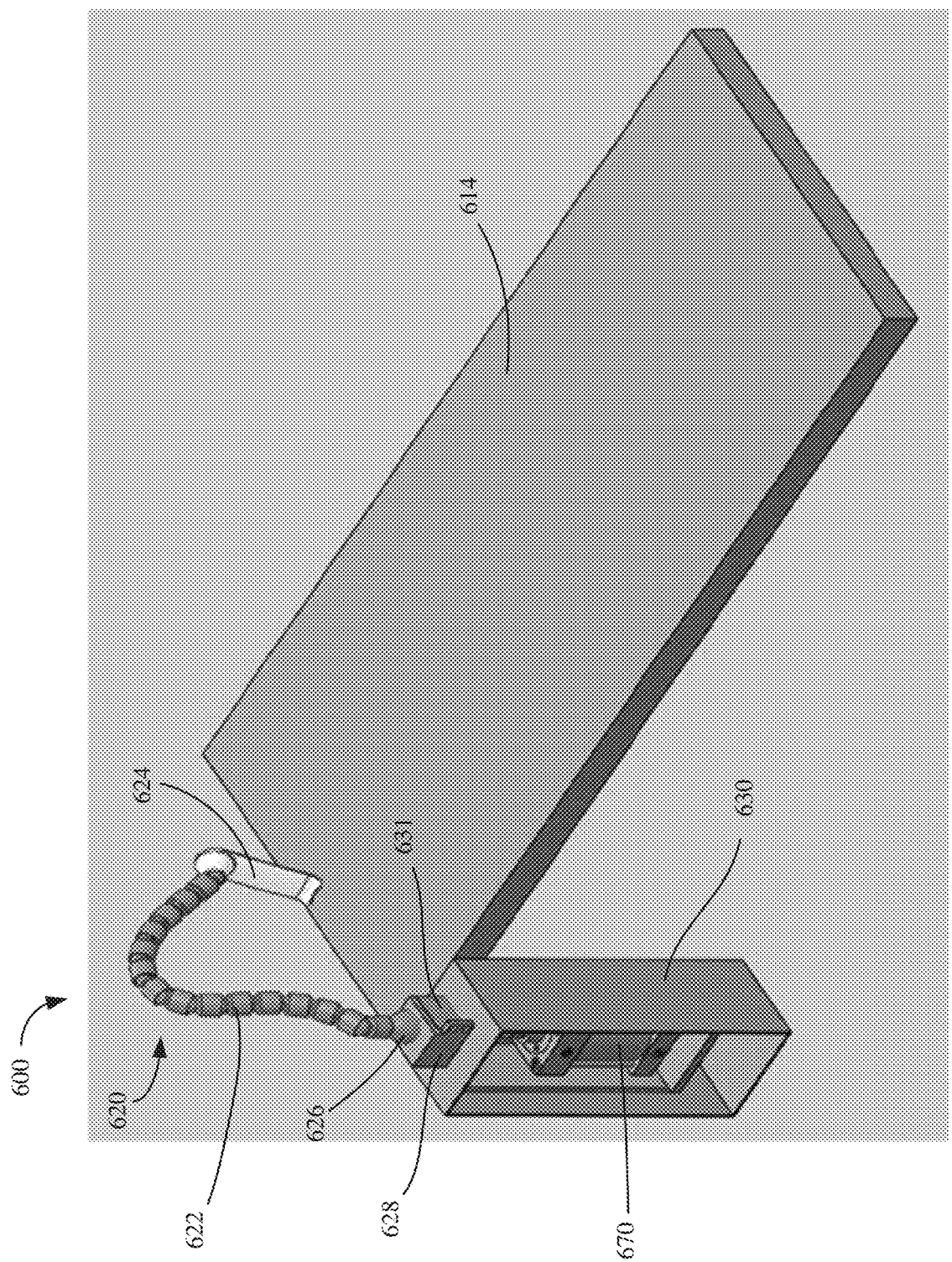
FIG. 32 shows another exemplary adjustable retaining arm system.

Additional feature and embodiments of the disclosed technology are illustrated in FIGS. 32-47. FIG. 32 shows another exemplary system 600 including a table 614, a control box 630 coupled to the table, and an adjustable retaining arm 620 coupled to the control box. The arm 620 comprises several segments 622, a distal tool adapter with retracted 624 attached, and proximal adapter components 626, 628 coupling the arm to a fixture 631 at the top of the box 630. A pneumatic motor 670 is also shown in the box 630.

FIGS. 33 and 34 show exemplary segments 622 of the arm 620. The segments 622 have a cylindrical main body 638 and a rounded convex head 640, with a neck 641 between. The body 638 has a concave recess 646 to receive the head 640 of an adjacent segment. Inside the segment is a longitudinal passage including a relative larger channel 647 within the main body and a relatively narrower channel 648 within the head 640, exiting at a rounded outlet 649. The radius of the head 640 can be between 0.3 inches and 1.0 inches, such as about 0.5 inches for example.

Figure 35:
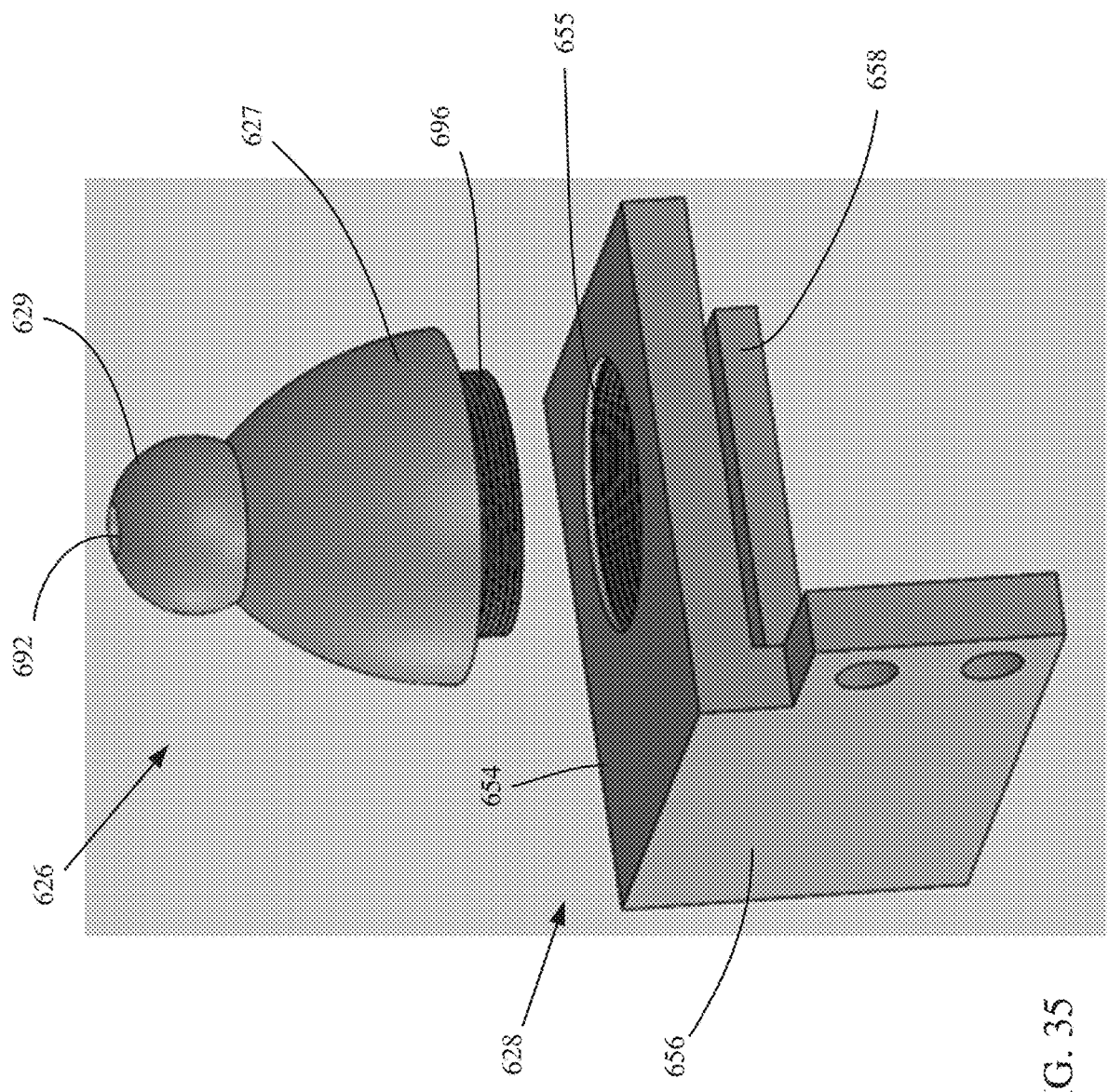
FIG. 35 is a perspective view of arm attachment component that couples an adjustable arm to a receiving component of an actuation and control unit.

FIG. 35 shows a proximal adapter 626 of the arm 620 and a mounting platform 628 that are threadably attachable together. The adapter 626 is at a proximal end of the arm, having a convex head 629 that couples to a concave recess 646 of an adjacent segment 620. The adapter 626 also has an enlarged base 627 and externally threaded portion 696 below the base. The platform 628 has a horizontal plate 654 with an internally threaded opening 655 that attaches to the externally threaded portion 696 to attach the adapter 626 to the platform 628. The platform further includes a vertical plate 656 and a lower horizontal plate 658 that couples the platform to a fixture 631 at the top of the control box 630. The arm 620 functions similarly to the other arms disclosed herein, using a tensioned cable running through the arm that is selective pulled on and released by a motor within the box 630. The threaded connection between 696 and 655 provides a more secure and stable connection between the arm and the box even when tension is released from the cable.

Figure 37:
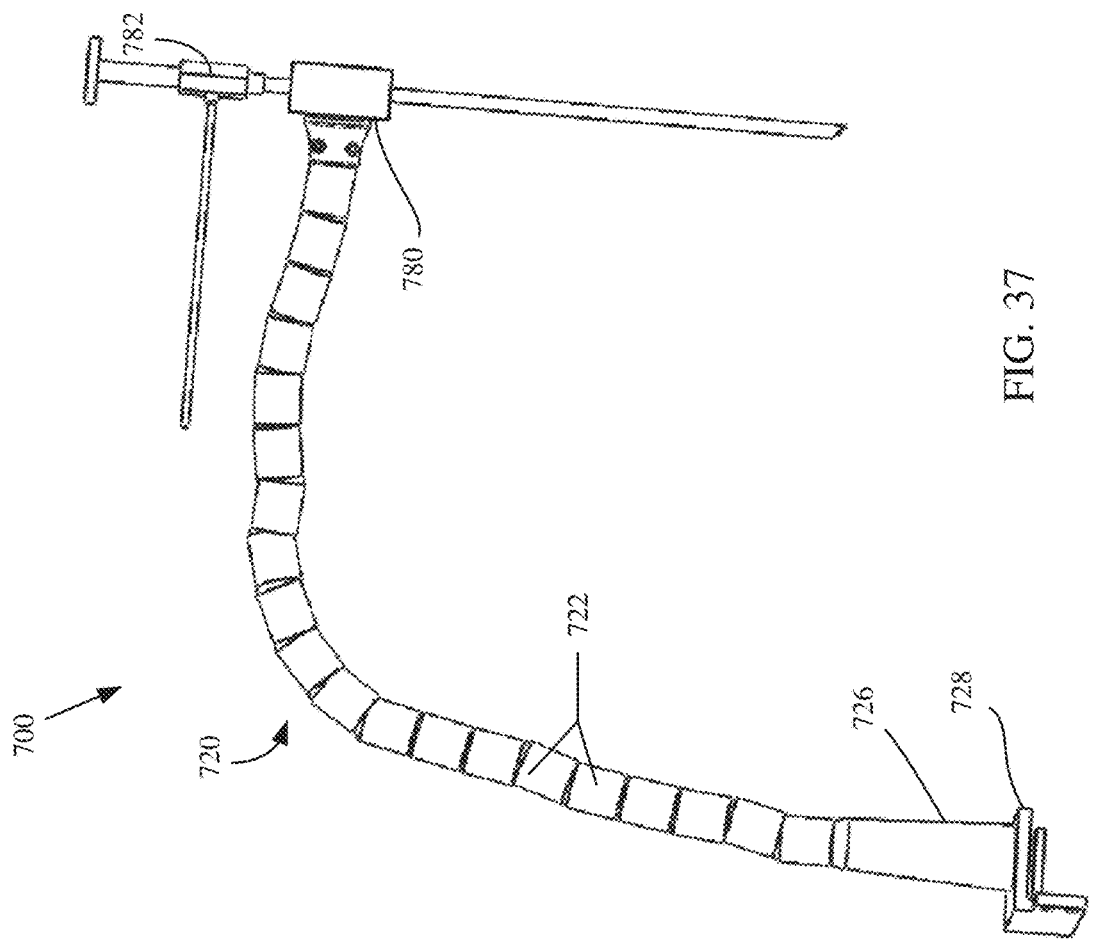
FIG. 37 shows the arm system of FIG. 36 with a laparoscopic tool attached.
Figure 36:
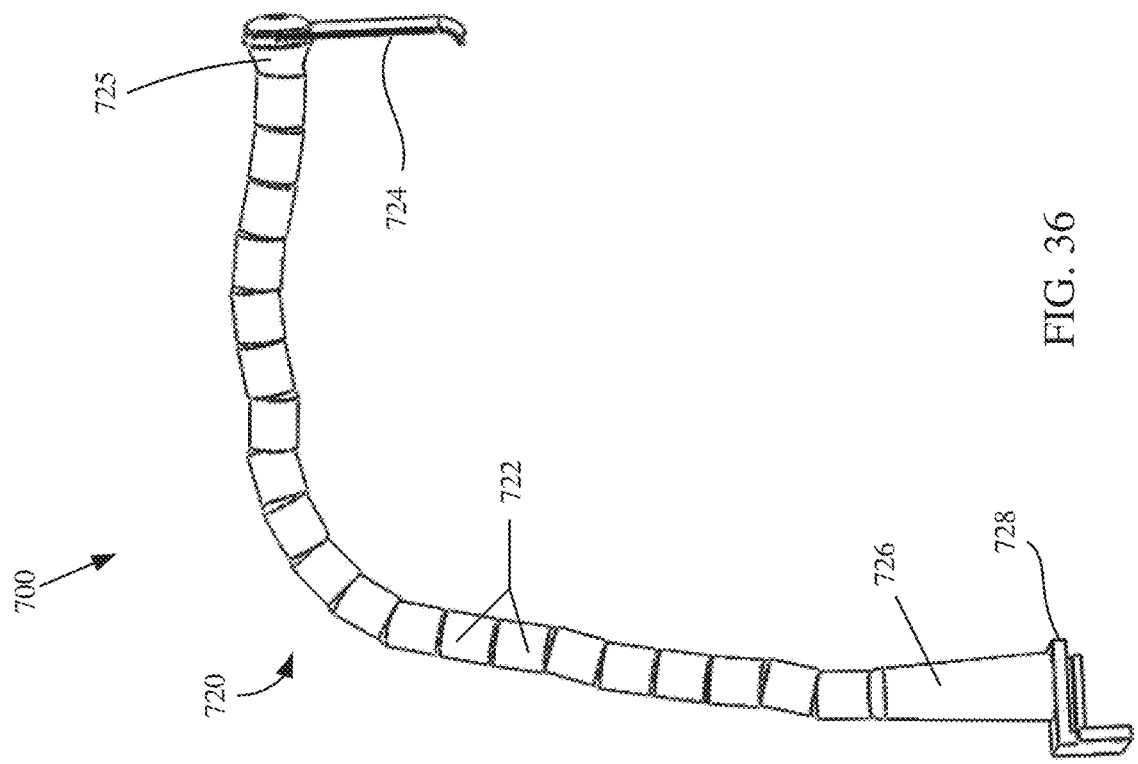
FIG. 36 shows another exemplary adjustable retaining arm system with a retractor tool attached.

FIGS. 36 and 37 show another exemplary retaining arm system 700, which includes an arm 720 comprising plural segments 722, an elongated proximal adapter 726, and platform 728. The elongated proximal adapter 726 (see FIG. 38) can include a lower threaded portion 796 that is coupled to the platform 728, as described with adapter 626 and platform 628, along with a tapered main body 727, rounded top 729, and passageway 792. The adapter 726 can have a length of between about 4 inches and about 12 inches, such as about 8 inches. The extended length of the adapter 726 can replace a few of the segments 722 and provide a permanently proximal rigid portion of the arm. This can reduce the demands on the tension cable, shortening the moment arm applied by loads on the distal end of the arm. The segments 722 (see FIG. 39) can have a cylindrical body 738 with a convex top surface 740 and a concave bottom recess 749, with a larger inner passageway 747 and narrower inner passageway 748 exiting at exit 749 in the convex end 740. The body 738 can have a radius of between 0.5 inches and 1.5 inches, such as about 0.75 inches or about 1.0 inches. The length of the segment can be between about 1.0 inches and about 2.0 inches, such as about 1.39 inches for example. The rounded ends can have a radius of curvature of between about 0.5 inches and about 1.0 inches, such as about 0.75 inches for example. This segment design can eliminate the neck feature present in other segment embodiments, thereby eliminating the stress concentrations that can occur in the neck when nigh tension and bending moments are applied to the arm. The design of the segments 722 can also be simpler and less expensive to manufacture.

In FIG. 36, a tool adapter 725 with retractor tool 724 is coupled to the distal end of the arm 720. In FIG. 37, a different tool adapter 780 with laparoscopic tool 782 is coupled to the distal end of the arm. FIG. 40 illustrates the tool adapter 780 in more detail, showing a base coupler 784 that couples to the end of the arm 720, a split body 786, and a passageway 788 for receiving a tool such a tool 782. The split body 786 can be loosened to enlarge the passageway 788 and then tightened with fasteners to secure the inserted tool. The two embodiments of FIGS. 36 and 37 illustrate how many different types of tools can be coupled to the distal end of the arm 720, using various different types of tool adapters.

The system 700 as well as other exemplary systems disclosed herein can be configured to provide adequate friction/locking between the segments to hold a relative high force (e.g., 20 lbs., 30 lbs., 40 lbs., etc.) at the distal end of the arm, using a relative long arm (e.g., 36", 40", 44" length). The arm can further be composed of light-weight, hygienic, disposable components that are low cost and simple to assembly and adjust. The arm segments can be comprised of any sufficiently rigid material (e.g., aluminum, steel, titanium, other metals or alloys, PMMA, PLA, FRPC, PEI, other polymeric materials, etc.) and can have interfaces of any geometry that provide sufficient frictional forces and/or locking between the segments. One exemplary material suitable for the arm segments is Edgetek (polyphenylene sulfide) manufactured by PolyOne Corporation. Some embodiments include roughened or sandblasted or bead-blasted surfaces, some include coatings such with high friction material like sandpaper or grit or carbinite material, some include inserts made of rubber or other malleable material, some include more rigid polymer inserts, some include O-ring inserts or O-rings mounted externally around the neck, some have other surface treatments. Some embodiments can provide a coefficient of friction between segments of at least 0.5 and/or at least 1.0.

Figure 43:
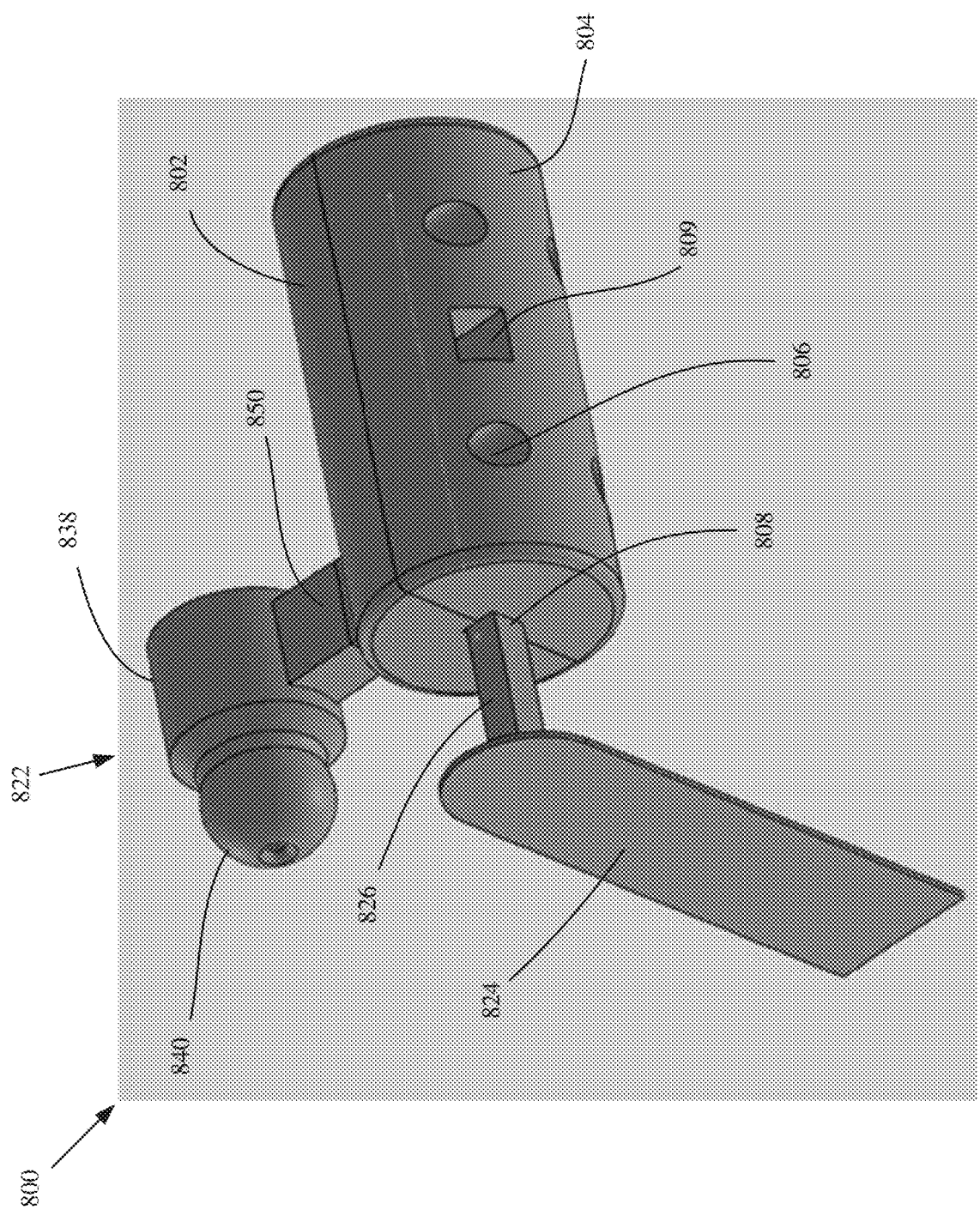
FIG. 43 shows the adapter of FIG. 41 with a retractor tool attached, and shows a component for coupling the adapter to the retaining arm.

FIGS. 41-43 show another exemplary tool adapter 800 that can be coupled to any of the adjustable retaining arms disclosed herein. The tool adapter 800 can include a ratchet mechanism that allow a tool to be quickly inserted and held securely without needing to loosen and tighten fasteners. FIG. 42 shows an internal ratchet component 810 that is mounted within two body halves 802, 804 of the adapter. A tool, such as tool 824 can have a stem 826 configured to be inserted into opening 808 of the tool adapter, such that the stem interfaces with a ratchet surface 812 of the component 810. The component 810 can be spring biased to hold the tool in the adapter, for example, such that when a button 814 is depressed, the ratchet surface 812 separates from the stem 826 within the tool adapter to release the stem so the tool can be removed. The tool adapter 800 can also comprise (see FIG. 43) an arm segment 822 with body 838 and head 840 coupled to the side of the tool adapter via connector 850. This can allow the tool adapter to be coupled to an arm either at the distal end or at an intermediate location between two other segments of the arm.

Figure 44:
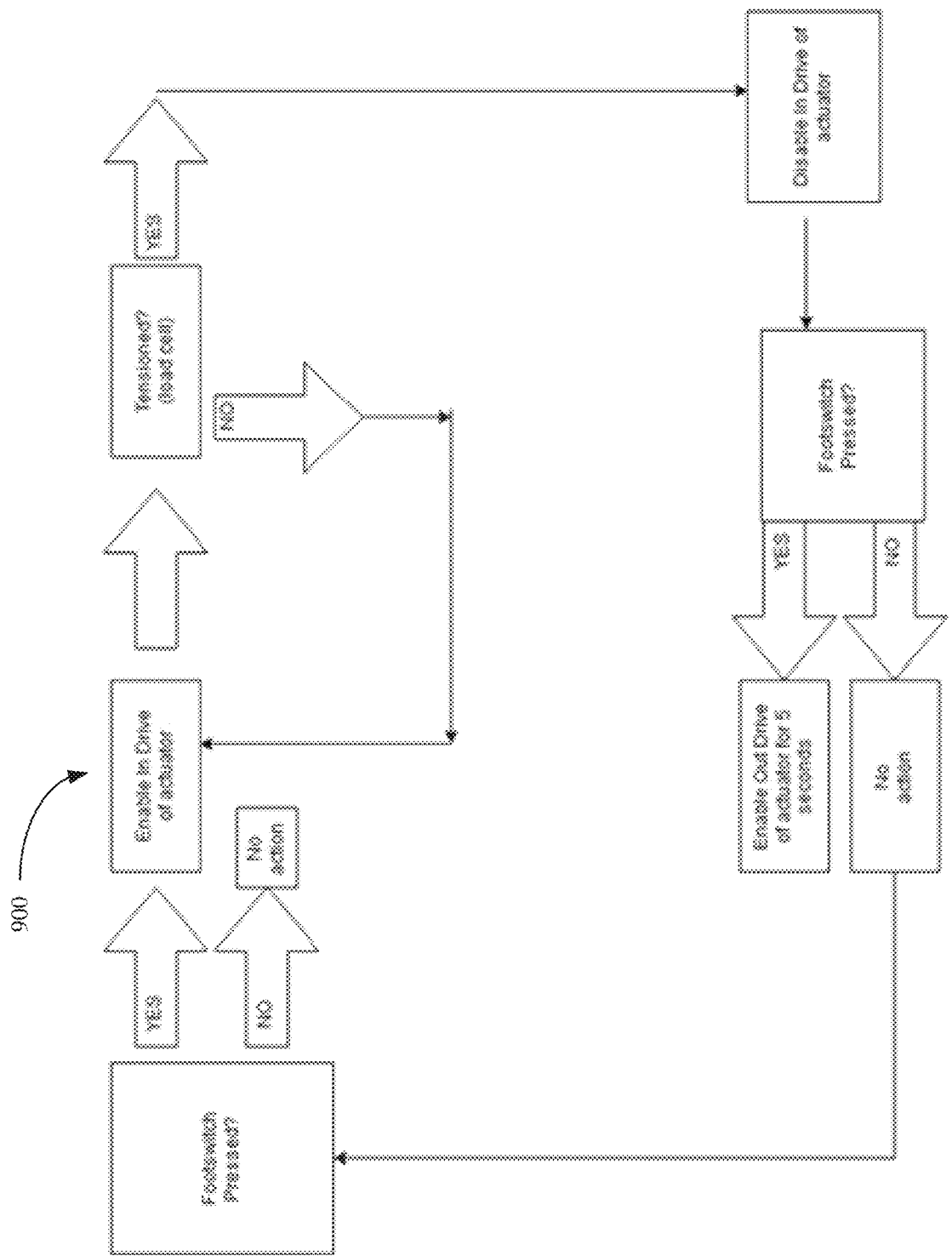
FIG. 44 is an exemplary logic diagram for a control system for an adjustable retaining arm system.

FIG. 44 is an exemplary logic diagram 900 for a control system for an adjustable retaining arm system. This logic system can control a linear actuator in the box that tensions the arm cable, for example. This logic can control the state toggling of the cable between a tensioned and un-tensioned state. After installing an arm and energizing the control unit, a user can start in the top left corner of the diagram of FIG. 44. The tool at the end of the un-tensioned arm can them be placed as desired (e.g., used to retract tissue into place by the surgeon), and then a footswitch can be pressed. When that occurs, power is supplied to the motor until a prespecified cable tension is achieved, and then the motor shuts off, representing the rigid arm state. The system again waits for a foot switch to be pressed (e.g., if the surgeon needs to reposition the arm), reversing the process by moving the motor outward for a specified time, and then the cycle repeats. During the tensioning phase, power can be supplied to the drive electronics whole simultaneously taking readings from a load cell or other sensor. When the prescribed preset tension is achieved, power to the drive system can be disabled, releasing tension on the cable.

Figure 45:
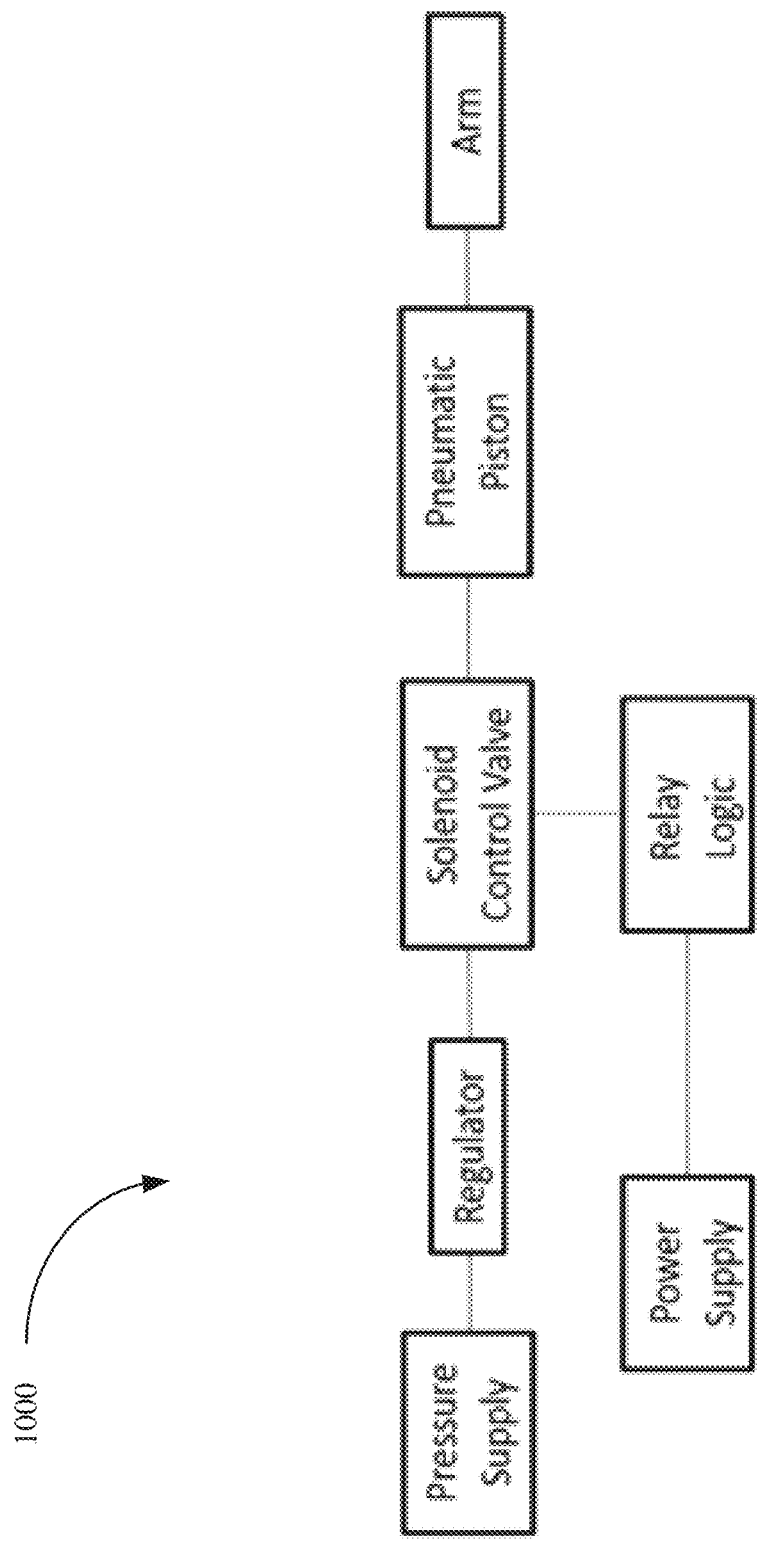
FIG. 45 is an exemplary schematic of a pneumatic system for an adjustable retaining arm system.

FIG. 45 is an exemplary schematic of a pneumatic system 1000 for an adjustable retaining arm system. A pneumatic actuation system 1000 can comprise a pneumatic actuator, a solenoid valve, a pressure regulator, and a relay circuit, as shown in FIG. 45. The pressure regulator can control the force applied to the cable, when considering the active area of the pneumatic cylinder.

Figure 46:
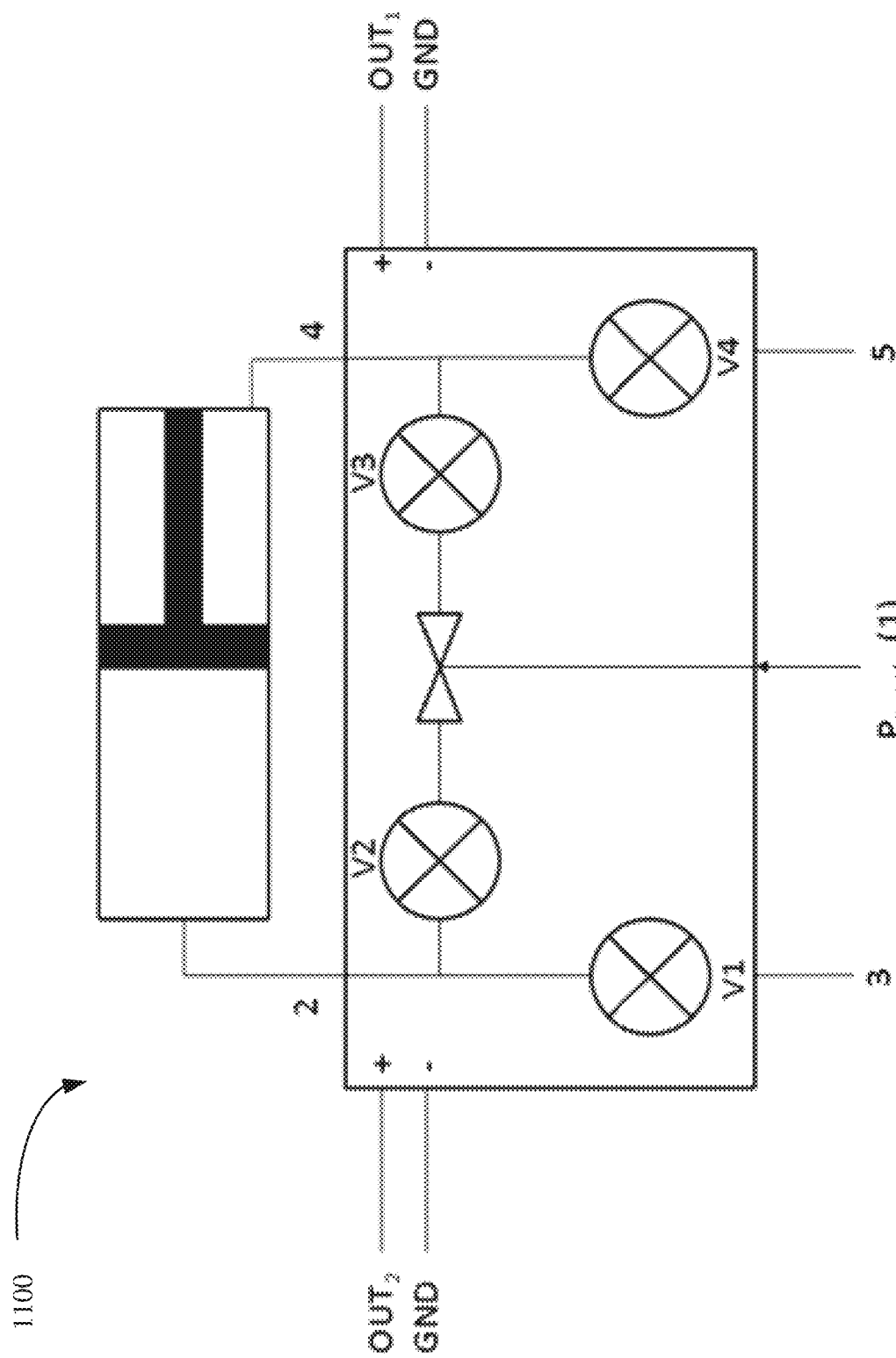
FIG. 46 is an exemplary pneumatic schematic for a solenoid valve and pneumatic actuator.

FIG. 46 is an exemplary pneumatic schematic 1100 for a solenoid valve and pneumatic actuator. The cylinder can be supplied air through the bi-directional, solenoid control valve, as shown in FIG. 46. A truth table for the solenoid valve is given in FIG. 47. From the truth table, Case 1 ("Off") is if the unit is not powered, Cases 2 ("Load") and 4 ("Button Press") are for attaching the arm or making it flexible, and Case 3 ("Run") is for when the arm is rigid. The solenoid valve can have a center exhaust position, meaning that all pressure is exhausted when electrical power is removed from the device.

Figure 48:
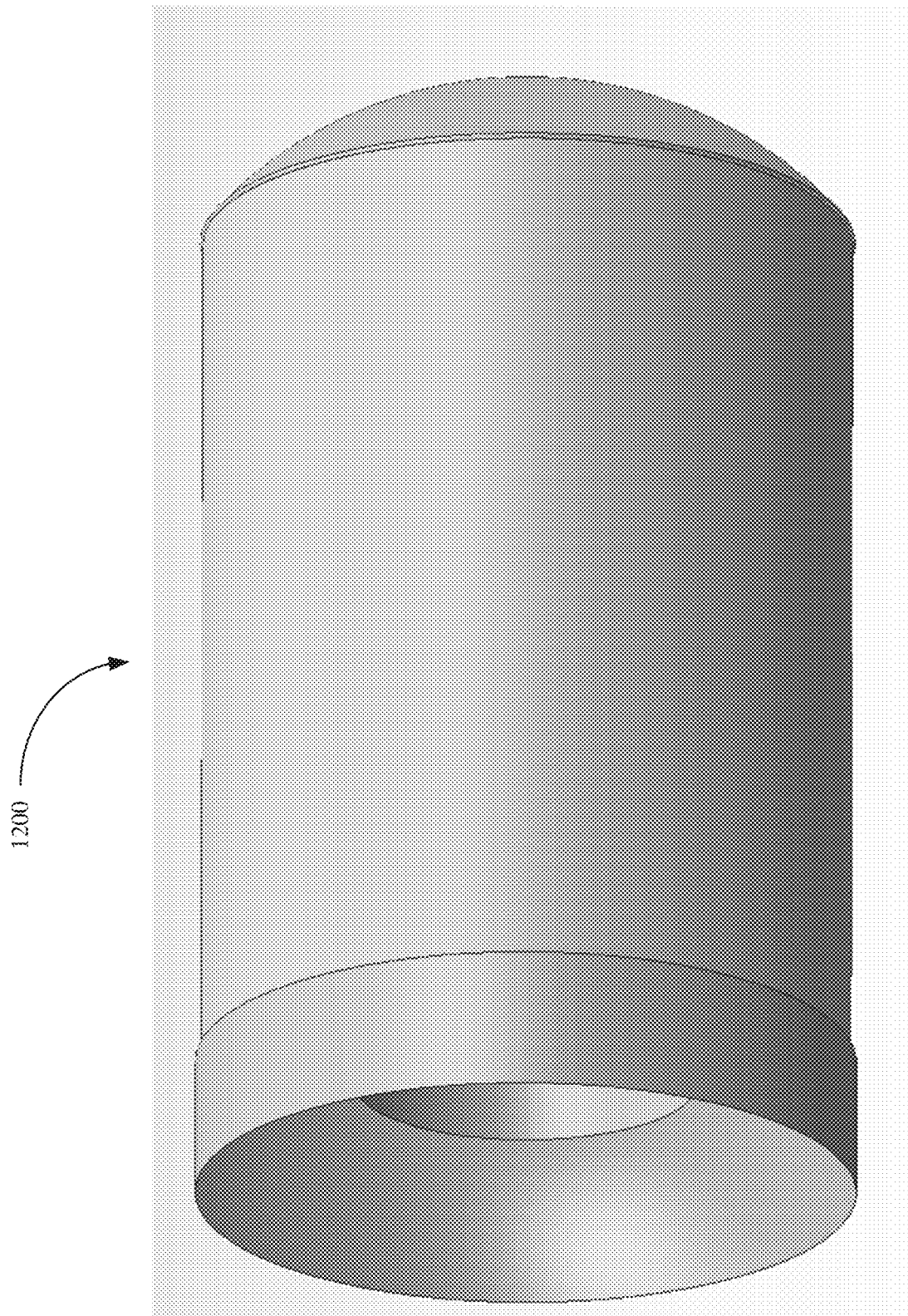
FIGS. 48 and 49 show a tubular arm segment that includes a polymeric insert in the end.
Figure 49:
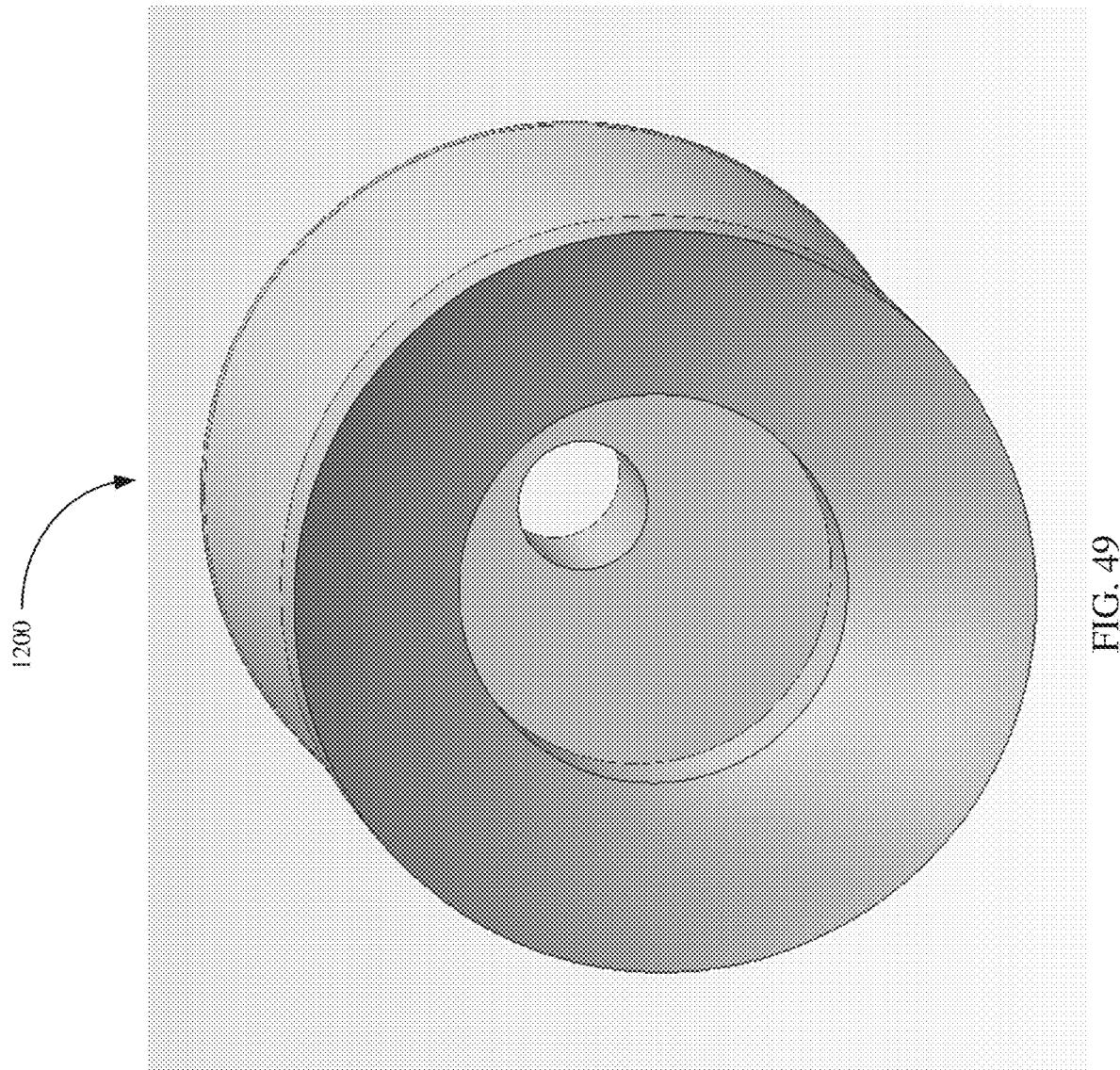

FIGS. 48 and 49 illustrate another exemplary arm segment 1200 that can be used with any of the adjustable retaining arm systems disclosed herein. The segment 1200 has a cylindrical outer surface with a convex distal surface and concave proximal surface, and a passageway through the middle, as in other arm segments disclosed herein. The segment 1200 can comprise multiple components, such as a relatively stronger, tubular, main body (such as formed of steel, stainless steel, aluminum, carbon fiber reinforced polymer, other composite, other metal, polymeric materials, etc.) and one or more a relatively less strong inserts that fit into proximal and distal cavities of the main body. The insert can comprise a compliant polymeric material, for example. The inserts can provide enhanced friction properties at the joints, can be simpler to manufacture, and/or provide other advantages. The inserts can be secured in the tubular main body with an adhesive, for example. The inserts can also be replaceable, such as when the friction surfaces wear out over time, and new inserts can be coupled to the same main body.

Figure 50:
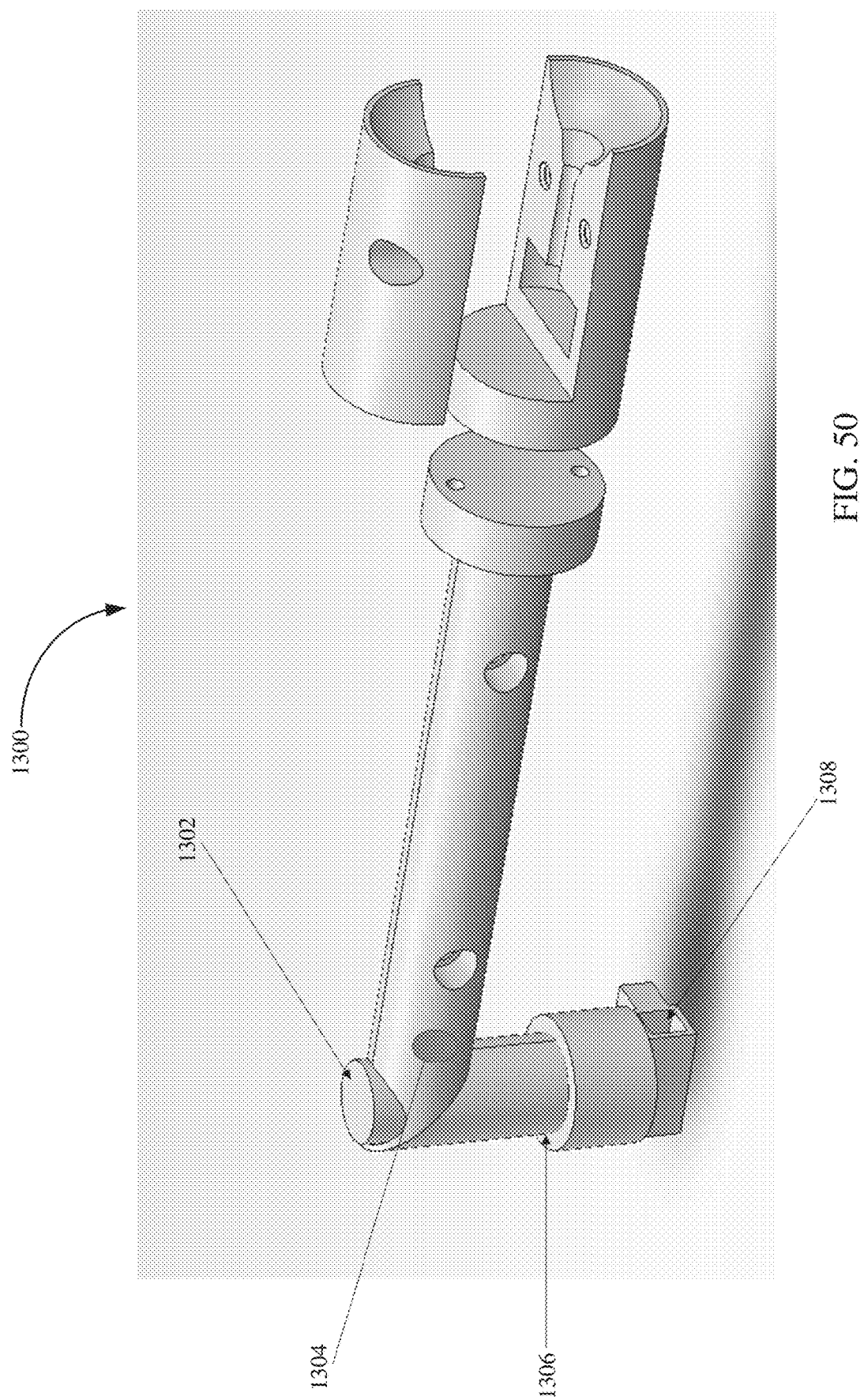
FIGS. 50 and 51 shows an exemplary tool attachment device that couples to the distal end of an adjustable retaining arm.
Figure 51:
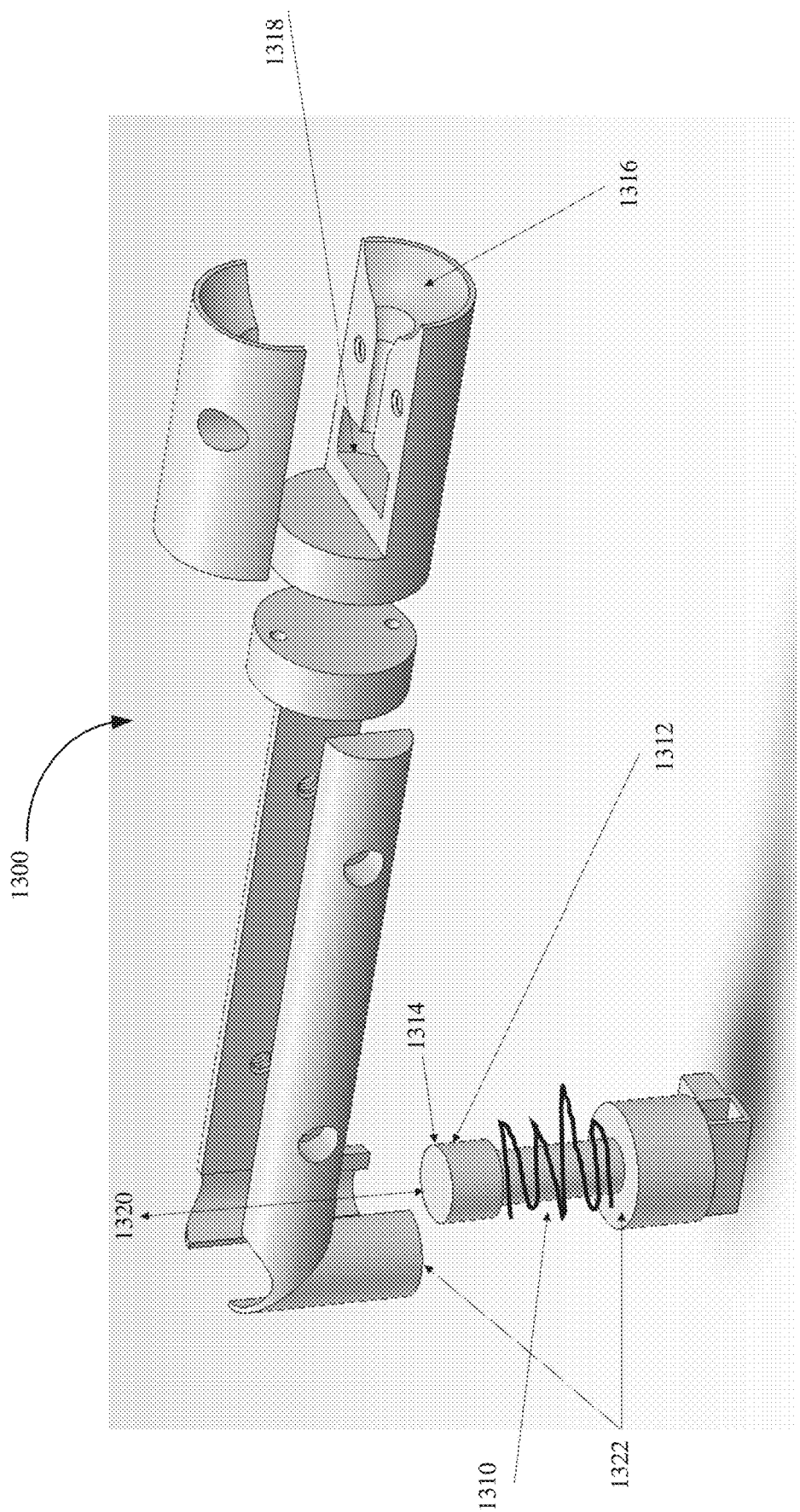

FIGS. 50 and 51 illustrate an exemplary tool attachment device 1300 can be coupled to the distal end of any of the adjustable retaining arm systems disclosed herein. The tool attachment device 1300 can have an opening 1308 for receiving a retractor tool, for example. A button at 1304, or elsewhere, can be user-actuated to release the tool from the opening 1308. The button or activator 1304 can be coupled to wires that snake through the device 1300 and back down to the arm to a power source. Another button or actuator at 1302, or elsewhere, can release the tool holder component 1306 so that its position can be adjusted, such as by turning, pivoting, swiveling, lengthening, etc., relative the rest of the device 1300 that is attached to the arm. As shown in FIG. 51, the adjustable joint 1322 can include a spring biasing mechanism 1310 that biases the tool holder component along axis 1320, so that the device is engaged and ready to use when the button 1302 is released. The spring 1310 can be retained by a cap 1312 that can be threaded on after the spring is in place. The cap 1312 can translate up and down in a fixed cylindrical cavity. The adjustable component 1306 and the fixed portion of the device 1300 can have interfacing surfaces that have mating splines (at 1322) to hold them in place when the button is released. The main body of the device 1300 can have a narrow diameter, such as under one inch, to reduce obstruction and simplify handling and reduce weight. A tool such as a retractor blade can project downwardly from the opening 1308, toward a patient surgical site. As shown in FIG. 51, the proximal end of the device 1300 can include an adapter for coupling to a distal end of an arm. A concave recess 1316 can mate with a convex head of the distal most arm segment, and an internal cavity 1318 can house a washer or retainer that retains the end of the tensioning cable. The cable goes through the last segment, through the washer/retainer, and terminates in the cavity 1318. There can be a nut or a braised or crimped end holding the washer/retainer on the cable, in some embodiments. The device 1300 is shown exploded into several pieces in FIGS. 50 and 51, though these pieces can all be assembled into a unit using fasteners or other components, with the end of the cable fixed inside the device 1300 securing the device to the arm.

For purposes of this description, certain aspects, advantages, and novel features of the embodiments of this disclosure are described herein. The disclosed methods, apparatus, and systems should not be construed as being limiting in any way. Instead, the present disclosure is directed toward all novel and nonobvious features and aspects of the various disclosed embodiments, alone and in various combinations and sub-combinations with one another. The methods, apparatus, and systems are not limited to any specific aspect or feature or combination thereof, nor do the disclosed embodiments require that any one or more specific advantages be present or problems be solved. Any of the features described herein in relation to any particular embodiment can be combined with any other features disclosed herein and/or included in any other embodiment disclosed herein, unless impossible or expressly stated otherwise.

Although the operations of some of the disclosed embodiments are described in a particular, sequential order for convenient presentation, it should be understood that this manner of description encompasses rearrangement, unless a particular ordering is required by specific language set forth below. For example, operations described sequentially may in some cases be rearranged or performed concurrently. Moreover, for the sake of simplicity, the attached figures may not show the various ways in which the disclosed methods can be used in conjunction with other methods.

As used in this application and in the claims, the singular forms "a," "an," and "the" include the plural forms unless the context clearly dictates otherwise. Additionally, the term "includes" means "comprises." Further, the term "coupled" generally means physically, mechanically, chemically, magnetically, and/or electrically coupled or linked and does not exclude the presence of intermediate elements between the coupled or associated items absent specific contrary language.

In view of the many possible embodiments to which the principles of the disclosed technology may be applied, it should be recognized that the illustrated embodiments are only preferred examples of the innovative technology and should not be taken as limiting the scope of the disclosure. Rather, the scope of the disclosure is at least as broad as the following claims. We therefore claim all that comes within the scope of these claims.

The invention claimed is:

1. An adjustable surgical retaining arm system comprising:
 a rigid support structure;

a cable tensioning device comprising a proximal cable receiver;

an arm comprising plural rigid arm segments arranged end-to-end along a longitudinal axis of the arm and forming articulation joints between adjacent axial ends of the arm segments, wherein the arm segments include axial passageways extending through the arm segments;

a cable extending through the axial passageways of the arm segments, the cable having a proximal end and a distal end;

a mounting platform coupled to a proximal end of the arm, the mounting platform configured to attach and detach a proximal end of the arm to and from the rigid support structure, the mounting platform configured to couple and decouple the proximal end of the cable to and from the proximal cable receiver of the cable tensioning device; and a surgical tool adapter coupled to a distal end of the arm and configured to hold a surgical tool, wherein the surgical tool adapter comprises:
  a distal cable receiver that is secured to the distal end of the cable;
  a tool holder configured to detachably couple a surgical tool to the surgical tool adapter; and
  an adjustable joint between the distal cable receiver and the tool holder operable to permit the tool holder to be fixed at any selected orientation of multiple different orientations relative to the distal cable receiver;

wherein the cable extends from the surgical tool adapter, through the arm, through the mounting platform, and through the rigid support structure to the cable receiver;

wherein the cable tensioning device is operable to move the cable receiver relative to the rigid support structure to adjust tension in the cable;

wherein the arm has an adjustable state when tension in the cable is less than an operative tension, wherein in the adjustable state the arm can be manually arranged in a desired position by articulation at the joints between the arm segments such that the surgical tool adapter can be placed in a desired position relative to a surgical patient; and wherein the arm has a rigid state when tension in the cable is at least the operative tension, wherein in the rigid state the tension in the cable applies axial compression along the arm segments and creates frictional resistance or mechanical interlocking in the joints between the arm segments that is sufficient to restrict the arm from articulating and holds the surgical tool adapter in the desired position.

2. The arm system of claim 1, wherein the adjustable joint includes a biasing spring that retains the joint in the selected orientation until a user compresses the biasing spring to release the adjustable joint.

3. The arm system of claim 2, wherein the adjustable joint further comprises splines that engage to fix the tool holder relative to the distal cable receiver when the biasing spring is released, and wherein the splines disengage to allow the tool holder to move from the selected orientation to another one of the multiple different orientations relative to the distal cable receiver when the biasing spring is compressed.

4. The arm system of claim 3, wherein the splines comprises a first set of splines fixed to the distal cable receiver and a second set of splines fixed to the tool holder, and wherein the first and second sets of splines mate with one other when engaged.

5. The arm system of claim 3, wherein the splines are arranged in a circular array.

6. The arm system of claim 2, wherein the adjustable joint allows the tool holder to pivot around an axis of the adjustable joint relative to the distal cable receiver when the biasing spring is compressed.

7. The arm system of claim 2, wherein the adjustable joint comprises an end cap and a button that are engaged with the biasing spring, wherein pressing the button compresses the biasing spring between the button and the end cap and disengages the adjustable joint.

8. The arm system of claim 1, wherein tool holder extends from the adjustable joint at a transverse angle relative to the distal cable receiver.

9. The arm system of claim 1, wherein the distal cable receiver comprises a concave surface that receives a convex surface of the distal most segment of the arm, wherein an interface between the concave surface and the convex surface allows the surgical tool adapter to be positionally adjustable relative to the distal most segment of the arm when the arm is in the adjustable state.

10. The arm system of claim 1, wherein the distal cable receiver comprises an internal cavity that houses a retainer that is coupled to and retains the distal end of the cable within the internal cavity.

11. An adjustable retaining arm system comprising:
a rigid support structure;
a cable tensioning system comprising a cable receiver and an actuator, wherein the cable tensioning system is supported by the rigid support structure;
an arm comprising:
  rigid arm segments arranged along a longitudinal axis of the arm and forming articulation joints between the arm segments;
  a cable extending through the arm segments;
  a proximal mounting platform coupled to a proximal end of the arm segments and configured to rapidly attach and detach the arm from the rigid support structure; and
  a surgical tool adapter configured to couple a surgical tool to the arm;
  wherein the cable extends from the tool adapter through the proximal mounting platform and through the rigid support structure to the cable receiver of the cable tensioning system; and
  wherein the proximal mounting platform is configured to couple and decouple a proximal end of the cable to and from the cable receiver;
a user input device; and
a control system configured to receive user input from the user input device and change the arm between at least an adjustable state and a rigid state by causing the actuator to move the receiver and thereby adjust the amount of tension that is applied to the cable by the cable tensioning system;
wherein in the adjustable state the arm can be arranged in a desired position by articulation at the joints between the arm segments such that the tool coupled to the tool adapter can be placed in a desired position relative to a patient, and in the rigid state the tension in the cable applies sufficient axial compression along the arm to restrict the arm from articulating and to hold the tool in the desired position; and
wherein the surgical tool adapter comprises:
  a distal cable receiver that is secured to a distal end of the cable;

a tool holder configured to detachably couple the surgical tool to the surgical tool adapter; and an adjustable joint between the distal cable receiver and the tool holder operable to permit the tool holder to be fixed at any selected orientation of multiple different orientations relative to the distal cable receiver.

12. The arm system of claim 11, wherein the adjustable joint includes a biasing spring that retains the joint in the selected orientation until a user compresses the biasing spring to release the adjustable joint.

13. The arm system of claim 12, wherein the adjustable joint further comprises splines that engage to fix the tool holder relative to the distal cable receiver when the biasing spring is released, and wherein the splines disengage to allow the tool holder to move from the selected orientation to another one of the multiple different orientations relative to the distal cable receiver when the biasing spring is compressed.

14. The arm system of claim 13, wherein the splines comprises a first set of splines fixed to the distal cable receiver and a second set of splines fixed to the tool holder, and wherein the first and second sets of splines mate with one other when engaged.

15. The arm system of claim 13, wherein the splines are arranged in a circular array.

16. The arm system of claim 12, wherein the adjustable joint allows the tool holder to pivot around an axis of the adjustable joint relative to the distal cable receiver when the biasing spring is compressed.

17. The arm system of claim 12, wherein the adjustable joint comprises an end cap and a button that are engaged with the biasing spring, wherein pressing the button compresses the biasing spring between the button and the end cap and disengages the adjustable joint.

18. The arm system of claim 11, wherein tool holder extends from the adjustable joint at a transverse angle relative to the distal cable receiver.

19. The arm system of claim 11, wherein the distal cable receiver comprises a concave surface that receives a convex surface of a distal most segment of the arm, wherein an interface between the concave surface and the convex surface allows the surgical tool adapter to be positionally adjustable relative to the distal most segment of the arm when the arm is in the adjustable state.

20. The arm system of claim 11, wherein the distal cable receiver comprises an internal cavity that houses a retainer that is coupled to and retains the distal end of the cable within the internal cavity.

* * * * *